(12) United States Patent
Yoshida et al.

(10) Patent No.: US 9,050,249 B2
(45) Date of Patent: Jun. 9, 2015

(54) ORAL PHARMACEUTICAL COMPOSITIONS IN TIMED-RELEASE PARTICLE FORM AND FAST-DISINTEGRATING TABLETS CONTAINING THIS COMPOSITION

(75) Inventors: Takayuki Yoshida, Tokyo (JP); Hiroaki Tasaki, Tokyo (JP); Masataka Katsuma, Tokyo (JP); Atsushi Maeda, Tokyo (JP)

(73) Assignee: ASTELLAS PHARMA INC., Tokyo (JP)

(*) Notice: Subject to any disclaimer, the term of this patent is extended or adjusted under 35 U.S.C. 154(b) by 2177 days.

(21) Appl. No.: 11/119,460

(22) Filed: Apr. 28, 2005

(65) Prior Publication Data

US 2005/0287211 A1 Dec. 29, 2005

Related U.S. Application Data

(60) Provisional application No. 60/567,301, filed on Apr. 30, 2004.

(51) Int. Cl.
| | | |
|---|---|---|
| *A61K 9/16* | (2006.01) | |
| *A61K 31/135* | (2006.01) | |
| *A61K 47/02* | (2006.01) | |
| *A61K 47/04* | (2006.01) | |
| *A61K 47/10* | (2006.01) | |

(Continued)

(52) U.S. Cl.
CPC ............ *A61K 9/0056* (2013.01); *A61K 9/2077* (2013.01); *A61K 9/2095* (2013.01); *A61K 9/5078* (2013.01); *A61K 31/135* (2013.01); *A61K 9/2081* (2013.01); *A61K 9/501* (2013.01); *A61K 9/5015* (2013.01); *A61K 9/5026* (2013.01); *A61K 9/5042* (2013.01); *A61K 9/5047* (2013.01)

(58) Field of Classification Search
CPC ........................... A61K 9/0056; A61K 9/2077
See application file for complete search history.

(56) References Cited

U.S. PATENT DOCUMENTS 4,844,905 A * 7/1989 Ichikawa et al. .............. 424/451
5,445,829 A * 8/1995 Paradissis et al. ............ 424/480

(Continued)

FOREIGN PATENT DOCUMENTS

| EP | 288 732 A2 | 11/1988 |
|---|---|---|
| JP | 09-188617 A | 7/1997 |

(Continued)

OTHER PUBLICATIONS

Remington's Pharmaceutical Sciences, 18th Edition, 1990, pp. 1635-1637.*

(Continued)

*Primary Examiner* — Rachael E Bredefeld

(74) *Attorney, Agent, or Firm* — Kilpatrick Townsend & Stockton LLP

(57) ABSTRACT

The present invention relates to an oral pharmaceutical composition in particle form, which comprises particles that contain a drug at the core of the pharmaceutical composition in particle form; a middle layer that contains two types of water-soluble components, an insolubilizer and an insolubilizing substance; and an outer layer for controlling water penetration that contains a water-insoluble substance. The present invention makes it possible to provide a pharmaceutical composition in particle form for oral use with which initial drug release is suppressed, the drug is quickly released thereafter, and lag time can be controlled as needed, and fast-disintegrating tablets containing this composition.

25 Claims, 6 Drawing Sheets

(51) Int. Cl.

| | |
|---|---|
| *A61K 47/12* | (2006.01) |
| *A61K 47/18* | (2006.01) |
| *A61K 47/24* | (2006.01) |
| *A61K 47/26* | (2006.01) |
| *A61K 47/32* | (2006.01) |
| *A61K 47/34* | (2006.01) |
| *A61K 47/36* | (2006.01) |
| *A61K 47/38* | (2006.01) |
| *A61K 47/40* | (2006.01) |
| *A61K 47/42* | (2006.01) |
| *A61K 9/00* | (2006.01) |
| *A61K 9/20* | (2006.01) |
| *A61K 9/50* | (2006.01) |

(56) References Cited

U.S. PATENT DOCUMENTS 5,560,913 A * 10/1996 Kupper .................. 424/732
5,910,319 A    6/1999 Anderson et al.
6,284,271 B1 * 9/2001 Lundberg et al. ........... 424/466

FOREIGN PATENT DOCUMENTS

JP    09-295933 A    11/1997
JP    2000-191519 A    7/2000
WO    WO90/06107    *  6/1990  ............... A61K 9/20

OTHER PUBLICATIONS

Banker et al, Modern Pharmaceutics, Fourth Edition, 2002, p. 100.*
Eeckman, et al., Effect of some physiological and non-physiological compounds on the phase transition temperature of thermoresponsive polymers intended for oral controlled-drug delivery; Int. J. Pharm., 2001, pp. 259-270; vol. 222, No. 2.
Ichikawa et al.; The Association of Powder Process Industry and Engineering; 1995; pp. 117-121.
PCT Search Report dated Jul. 5, 2005.
Frederic Eeckman, et al.; Effect of some physiological and non-physiological compounds on the phase transition temperature of thermoresponsive polymers intended for oral controlled-drug delivery; International Journ. of Pharmaceutics; 222 (2001) 259-270.
T. Yoshida, et al.; Salting-out taste-masking system generates lag time with subsequent immediate release; International Journ. of Pharmaceutics, 365 (2009) 81-88.
Tatsu Nakano, et al.; Suppression of Agglomeration in Fluidized Bed Coating. III. Hofmeister Series in Suppression of Particle Agglomeration; Pharmaceutical Research, vol. 126, No. 10, 1999.

* cited by examiner

ORAL PHARMACEUTICAL COMPOSITIONS IN TIMED-RELEASE PARTICLE FORM AND FAST-DISINTEGRATING TABLETS CONTAINING THIS COMPOSITION

This application claims the benefit of priority to U.S. Provisional Patent Application No. 60/567,301, filed Apr. 30, 2004, the teachings of which are incorporated by reference in their entireties for all purposes.

TECHNICAL FIELD

The present invention relates to an oral pharmaceutical composition in timed-release particle form and fast-disintegrating tablets containing this composition. In further detail, the present invention relates to an oral pharmaceutical composition in particle form with a multi-layered structure, which comprises particles that contain a drug at the core of the pharmaceutical composition in particle form; a middle layer that contains two types of water-soluble components, an insolubilizer and an insolubilizing substance; and an outer layer for controlling water penetration that contains a water-insoluble substance, this oral pharmaceutical composition in timed-release particle form being such that a layer for controlling water penetration controls the speed at which water penetrates to inside the particles and an insolubilizer makes it possible to temporarily prevent dissolution of an insolubilizing substance, as well as fast-disintegrating tablets containing this composition.

PRIOR ART

Granules, fine granules, powders, and other oral pharmaceutical compositions in particle form are a preparation form that can be easily taken, even by patients who have difficulty swallowing tablets and capsules, because they are smaller than tablets and capsules. Moreover, attention has recently been focused on preparation forms that are very convenient for a patient to take, and of these, fast-disintegrating tablets are very convenient because they can be taken without water and they are easy to swallow.

However, oral pharmaceutical compositions in particle form are smaller than tablets and capsules. Therefore, the surface area per weight thereof is large and the surface area that contacts water in vivo after administration is large. Consequently, the speed at which water penetrates these compositions is fast and various problems occur when the drug is quickly released in the oral cavity after the composition is taken. For instance, if the drug has an unpleasant taste, the patient will notice the very unpleasant taste once the drug has been quickly released in the oral cavity and compliance will drop considerably. Moreover, there will be a variety of problems if the drug is absorbed in the oral cavity, including the fact that there will be an increase in individual differences in terms of adverse events and pharmacological effects once the drug has been quickly released in the oral cavity.

In order to solve the above-mentioned problems, it is necessary to suppress for a specific time oral drug release from an oral pharmaceutical composition in particle form. For instance, the unpleasant taste of a drug can be masked by suppressing dissolution of the drug for the specific time the oral pharmaceutical composition in particle form is inside the oral cavity. Moreover, it is possible to prevent an increase in individual differences in terms of adverse events and pharmacological effects and other problems from occurring as a result of the drug being absorbed in the oral cavity by suppressing drug dissolution for the specific time the oral pharmaceutical composition in particle form is inside the oral cavity.

On the other hand, the drug must be released from the oral pharmaceutical composition in particle form and a sufficient amount of the drug must be absorbed in vivo in order to realize to the fullest pharmacological effects. Most drugs are absorbed in the upper gastrointestinal tract. Moreover, pharmaceutical preparations move through the gastrointestinal tract over time. Taking these points into consideration, it is preferred that once drug release from an oral pharmaceutical composition in particle form has been suppressed for a specific time, the drug be quickly released before the oral pharmaceutical composition in particle form moves to the lower gastrointestinal tract so that it will be absorbed by the upper gastrointestinal tract.

Consequently, (1) it is necessary to suppress drug release for a specific time inside the oral cavity in order to mask the unpleasant taste of the drug, prevent absorption of the drug in the oral cavity, and the like, and (2) it is preferred that the drug be quickly released from the oral pharmaceutical composition in particle form in the gastrointestinal tract in order to realize to the fullest the pharmacological effects. Furthermore, the extent of the unpleasant taste and the time the taste remains and the absorption speed of the drug is absorbed in the oral cavity vary with the drug, and the time for which the preparation is retained in the oral cavity, and the like vary with the pharmaceutical preparation; therefore, (3) it is preferred that it be possible to control the length of time for which drug release is suppressed (lag time hereafter) as desired in accordance with the properties of the drug and pharmaceutical preparation. Satisfying these three objectives ultimately requires a profile whereby once drug release has been suppressed for a specific time, the drug is quickly released, as well as control of this profile as needed.

Moreover, fast-disintegrating tablets containing a pharmaceutical composition in particle form with which release of a drug is controlled are a way of controlling release of a drug for a variety of purposes. In addition the pharmaceutical composition in particle form that is contained in this fast-disintegrating tablet must be smaller than granules, fine granules, powders, and other oral pharmaceutical compositions in particle form in order to reduce the gritty sensation in the oral cavity. Nevertheless, when this pharmaceutical composition in particle form is are smaller, it is more difficult to simultaneously realize the above-mentioned three objectives because the drug is released more quickly.

It is virtually impossible to simultaneously (1) suppress initial drug dissolution, (2) realize fast drug release thereafter, and (3) control the lag time of this type of oral pharmaceutical composition in particle form or oral pharmaceutical composition in particle form for fast-disintegrating tablets with conventional methods. Means whereby a pharmaceutical preparation containing a drug is coated with a variety of bases are used in order to control drug release from a pharmaceutical preparation. For instance, when a pharmaceutical preparation containing a drug is coated with only a water-insoluble substance, the speed with which water penetrates to inside the pharmaceutical preparation can be controlled and initial drug dissolution can be suppressed. However, the water penetration speed and drug release speed are kept under control by this means; therefore, the drug cannot be quickly released after a lag time. Vice-versa, when fast drug release is accomplished by reducing the amount of coating, the water penetration speed cannot be controlled and initial drug dissolution cannot be suppressed. It is difficult to realize fast drug release after suppressing initial drug release by this type of coating with a water-insoluble substance only, regardless of the pharmaceutical preparation size or the amount of coating. In the end, of the three objectives, it is not possible to simultaneously (3) control lag time while (1) suppressing initial drug dissolution and (2) realizing fast drug release thereafter.

Therefore, methods whereby a pharmaceutical preparation containing a drug is coated with a mixed layer of a water-insoluble substance and a water-soluble substance are generally used for fast drug release once initial drug dissolution has been suppressed (Patent Reference 1). It is possible to control the speed at which water penetrates to inside the pharmaceutical preparation and suppress initial drug dissolution until the water-soluble substance in the mixed layer dissolves. When the water-soluble substance in the layer dissolves, fine holes form in the layer and the water penetration speed is accelerated; therefore, fast drug release can be realized. In the end, of the three objectives, the two objectives of (1) suppressing initial drug dissolution and (2) fast drug release thereafter can be accomplished. However, there is not sufficient drug release from the layer in which fine holes have formed and the drug release speed after a lag time is relatively slow by this means. Therefore, fast drug release after a lag time cannot be realized when the amount of coating is increased in an attempt to prolong lag time in order to accomplish three objectives. Moreover, when the amount of water-soluble substance in the mixed layer is increased in an attempt to realize fast drug release, it becomes difficult to suppress the drug release speed, and when the amount of coating is increased to realize a certain lag time, it is still impossible to obtain fast drug release. It is ultimately impossible to satisfy the third objective of (3) controlling lag time with a mixed layer coating of a water-insoluble substance and a water-soluble substance.

Thus, it is difficult to simultaneously solve the three objectives by simply coating a pharmaceutical preparation containing a drug with one layer. Therefore, a fast-release particle product of two layers coated on core particles containing a drug is disclosed in Patent Reference 2. Fast drug release is accomplished simply by using a mixed layer of a water-insoluble substance and water-soluble substance, but initial drug release cannot be sufficiently controlled; therefore, by means of this invention the pharmaceutical preparation is coated with a second layer of a water-soluble substance on top of the mixed layer so that initial drug release can be suppressed. Nevertheless, according to the knowledge of the inventors, a longer lag time is needed in order to accomplish the purpose of the pharmaceutical preparation. Moreover, although it is never mentioned in the patent, it is difficult to control lag time.

Consequently, a purpose of the present invention is to provide an oral pharmaceutical composition in particle form and fast-disintegrating tablets containing this composition with which pharmaceutical compositions in particle form that were designed to be used for oral administration can have a sufficiently long lag time, drug can be quickly released after the lag time, and the length of the lag time can be controlled as needed in accordance with the properties and purpose of the drug and pharmaceutical preparation. Other purposes of the present invention will become clear from the citations in the present Specification.

[Patent Reference 1] International Publication 02/96392 Pamphlet (Specification of U.S.P. 2003/096791)

[Patent Reference 2] JP (Kokai) 2000-191519

DISCLOSURE OF THE INVENTION

In light of these circumstances, the inventors performed intense studies focusing on the fact that means for coating core particles containing a drug with two layers that clearly have different roles may be effective. As a result, they discovered that the above-mentioned three objectives can be simultaneously accomplished with an oral pharmaceutical composition in particle form with a multi-layered structure, which comprises particles that contain a drug at the core of the pharmaceutical composition in particle form; a middle layer that contains two types of water-soluble components, an insolubilizer and an insolubilizing substance; and an outer layer for controlling water penetration that contains a water-insoluble substance. That is, they discovered that when a pharmaceutical composition in particle form is obtained by coating core particles containing a drug with a middle layer that will not dissolve for a certain time and will quickly dissolve thereafter and further coating these particles with a layer that controls the amount of water penetration by controlling the speed with which water penetrates inside the pharmaceutical compositions, it is possible to have a sufficiently long lag time and to release drug quickly after the lag time, and it is possible to control lag time to within a length of 2 to 20 minutes by varying the amount of coating and the components of each coating layer.

Consequently, the first characteristic of the present invention is a middle layer made from a water soluble substance that will quickly dissolve after a lag time but will remain insoluble for a specific time. Thus far, a balance between lag time formation and fast drug release has been pursued using a combination of a water-insoluble substance and a water-soluble substance. However, the inventors considered that the use of a combination wherein one water-soluble substance renders insoluble another water-soluble substance is in some way related to the solution to the above-mentioned objectives. That is, the inventors believed that a layer that suppresses drug dissolution is temporarily formed by dissolution of one water-soluble substance (insolubilizer) to promote insolubilization of the other water-soluble substance (insolubilizing substance) and then once the insolubilizer was completely released, the insolubilizing substance will recover the original water solubility thereof, making fast drug release possible.

One example of the insolubilizer and insolubilizing substance used for this purpose is the following salting out-type insolubilizer and salting out-type insolubilizing substance.

The salting out-type insolubilizing substance in the present invention refers to a group of substances that includes polymers having an LCST in water (lower critical solution temperature, Kagaku Daijiten (Tokyo Kagaku Dojin)) (abbreviated as LCST polymer hereafter). Moreover, salting out-type insolubilizer refers to a group of substances that include the "water-soluble salts" listed hereafter. LCST polymers will dissolve in water at a certain temperature or lower, but will not dissolve in water at a certain temperature or higher, and solubility thereof changes reversibly with a change in temperature. As cited in the reference *International Journal of Pharmaceutics*, 222, 259-270 (2001), solubility in water of an LCST polymer changes reversibly, even when a certain water-soluble salt is added. In other words, when a water-soluble salt is added to an aqueous solution in which an LCST polymer has been dissolved, the LCST polymer separates from the aqueous phase and precipitates to become insoluble. Moreover, when the water-soluble salt is removed, the LCST polymer dissolves in water once again. Consequently, when particles containing a drug are coated with a layer composed of a salting out-type insolubilizer (water-soluble salt) and a salting out-type insolubilizing substance (LCST polymer), insolubilization of the salting out-type insolubilizing substance is promoted by the salting out-type insolubilizer that has already been dissolved in the water by using this phenomenon. The speed with which water penetrates inside the particles is suppressed by the layer of salting out-type insolubilizing substance that has formed as a result, and a lag time forms during which the drug is not released. Once all of the coated salting out-type insolubilizer has been dissolved and released thereafter, the salting out-type insolubilizing substance dissolves in the water. The inventors believed that the drug could probably be quickly released as a result. However, the salting out-type insolubilizer and salting out-type insolubilizing substance both are very water soluble, and it was therefore estimated that even when a pharmaceutical composition in particle form is coated with this insolubilizer and this substance, both will quickly dissolve and it will not be possible to suppress initial drug release. The inventors actually proved that it is impossible to form a sufficient lag time for pharmaceutical compositions in particle form simply by coating core particles with a layer composed of a salting out-type insolubilizer and a salting out-type insolubilizing substance as described by FIG. 1 of Experimental Method 1.

When the inventors therefore conducted intense studies in order to form the desired lag time, they focused on further coating the particles with a layer for controlling the amount of water that penetrates the particles, which is the second characteristic of the present invention. In short, they discovered that a lag time sufficient for pharmaceutical compositions in particle form can be formed by coating core particles containing a drug not only with a middle layer composed of an insolubilizer and an insolubilizing substance, but also a layer for controlling water penetration. The inventors considered that the speed with which water penetrates the inside of a pharmaceutical preparation is controlled by coating the outside of the middle layer of a pharmaceutical composition with a layer for controlling water penetration composed of primarily a water-insoluble substance; as a result, insolubilization of the middle layer temporarily proceeds slowly and a long lag time is formed. The inventors proceeded with further intense study and discovered that in addition to forming a sufficient lag time, the drug is quickly released after the lag time by increasing the amount of coating of the middle layer to a certain extent and decreasing the amount of coating of the layer for controlling water penetration. This is because the middle layer components quickly dissolve once they have been temporarily rendered insoluble; as a result, even if there is a large amount of coating, a fast drug release speed is realized after a lag time. Furthermore, the layer for controlling water penetration is composed primarily of a water-insoluble substance; therefore, although the drug release speed is low when there is a large amount of coating, a small amount of coating is sufficient in the present invention and it is possible to avoid prolonging the drug release speed after a lag time because of this small amount of coating. Moreover, the inventors discovered that by means of the present invention, it is possible to control as needed the length of the lag time in accordance with the purpose of the pharmaceutical composition by changing the amount of coating and components in the middle layer and the amount of coating and components in the layer for controlling water penetration.

The inventors performed intense studies of the pharmaceutical composition in particle form with emphasis on the components of the middle layer ideal for realizing the above-mentioned temporary insolubilization. As a result, they found that it is possible to simultaneously solve the above-mentioned three objectives without limiting the components of the middle layer to the above-mentioned combination of a water-soluble salting out-type insolubilizer and water-soluble salting out-type insolubilizing substance by using a middle layer that is a combination of another type of insolubilizer and insolubilizing substance. In other words, they discovered that even if an insolubilizer and insolubilizing substance other than the above-mentioned that are water-soluble and satisfy certain properties are used in combination with one another, the pharmaceutical composition in particle form where core particles containing a drug are coated with a middle layer composed of this combination and further coated with a layer for controlling water penetration are capable of simultaneously solving the above-mentioned three objectives. For instance, the middle layer components are not limited to a combination of the above-mentioned salting out-type insolubilizer (water-soluble salt, and the like) and salting out-type insolubilizing substance (LCST polymer, and the like). The objectives of the present invention can be accomplished by using a combination of a temperature-type insolubilizer and a temperature-type insolubilizing substance with which insolubilization occurs by changing ambient temperature. Moreover, the objectives of the present invention can be similarly accomplished with a combination of a pH-type insolubilizer and a pH-type insolubilizing substance using insolubilization as a result of pH changes. In other words, as long as both the insolubilizer and insolubilizing substance are water-soluble and the insolubilizer has the ability to render the insolubilizing substance insoluble, it is possible to simultaneously solve the three objectives of (1) suppressing initial drug release, (2) fast drug release after a lag time, and (3) controlling lag time, regardless of the theory behind the insolubilization. On the other hand, the layer for controlling water penetration is applied for the purpose of controlling the speed with which water penetrates to inside the pharmaceutical composition in particle form; therefore, there are no limitations to the components thereof.

The present invention was completed as a result of proceeding with further study based on this knowledge, and relates to 1. an oral pharmaceutical composition in timed-release particle form, which comprises particles that contain a drug at the core of the pharmaceutical composition in particle form; a middle layer that contains two types of water-soluble components, an insolubilizer and an insolubilizing substance; and an outer layer for controlling water penetration speed that contains a water-insoluble substance;

2. a masked oral pharmaceutical composition in particle form, which comprises particles that contain a drug at the core of the pharmaceutical composition in particle form; a middle layer that contains two types of water-soluble components, an insolubilizer and an insolubilizing substance; and an outer layer for controlling water penetration speed that contains a water-insoluble substance;

3. the pharmaceutical composition in particle form according to claim 1 or 2, wherein the middle layer comprises a salting out-type insolubilizer and a salting out-type insolubilizing substance;

4. the pharmaceutical composition in particle form cited in claim 3, where the salting out-type insolubilizer is one or more selected from a group of substances with a $\Delta CST_1$ of 10° C. or higher;

5. the pharmaceutical composition in particle form cited in claim 4, where the salting out-type insolubilizer is one or more selected from the group of substances consisting of sodium carbonate, monobasic sodium phosphate, dibasic sodium phosphate, sodium metaphosphate, trisodium phosphate, potassium bicarbonate, sodium bicarbonate, sodium polyphosphate, sodium pyrophosphate, sodium chloride, potassium chloride, sodium sulfate, sodium sulfite, sodium citrate, dibasic sodium citrate, monosodium glutamate, disodium succinate, glycine, alanine, sorbitol, xylitol, inositol, sucrose, glucose, and fructose, and hydrates thereof;

6. the pharmaceutical composition in particle form cited in any one of claims 2 through 5, where the salting out-type insolubilizing substance is one or more selected from a group of substances having a $CST_2$ of 55° C. or lower and a $CST_3$ of 37° C. or higher;

7. the pharmaceutical composition in particle form cited in any one of claims 2 through 5, where the salting out-type insolubilizing substance is one or more selected from a group of mixtures having as individual substances a $CST_2$ of 55° C. or higher and/or $CST_3$ of 37° C. or lower, but having as a mixture of two or more substances a $CST_2$ of 55° C. or lower and a $CST_3$ of 37° C. or higher;

8. the pharmaceutical composition in particle form cited in claim 6 or claim 7, where the salting out-type insolubilizing substance is one or more selected from the group of substances consisting of hydroxypropylmethylcellulose, hydroxypropylcellulose, methylcellulose, polyvinyl alcohol-polyethylene glycol graft copolymer, carboxyvinyl polymer, polyvinyl alcohol, polyethylene oxide, povidone, copolyvidone, polyoxyethylene hydrogenated castor oil, polymers containing N-isopropylacrylamide and derivatives where hydrophobic groups have been introduced to the N position of acrylamide, and polyoxyethylene polyoxypropylene glycol;

9. the pharmaceutical composition in particle form cited in claim 1 or claim 2, where the middle layer comprises an acid-type insolubilizer and an acid-type insolubilizing substance;

10. the pharmaceutical composition in particle form cited in claim 9, where the acid-type insolubilizer is one or more selected from a group of substances with a pH of 5 or lower;

11. the pharmaceutical composition in particle form cited in claim 10, where the acid-type insolubilizer is selected from the group consisting of dibasic sodium citrate, monobasic sodium phosphate, citric acid, malic acid, and tartaric acid, and hydrates thereof;

12. the pharmaceutical composition in particle form cited in any one of claims 9 through 11, where the acid-type insolubilizing substance is one or more selected from a group of substances that will dissolve in a test fluid that simulates the inside of the oral cavity, but will not dissolve in a test fluid with a pH of 5 or lower;

13. the pharmaceutical composition in particle form cited in claim 12, where the acid-type insolubilizing substance is one or more selected from the group of substances consisting of carboxymethylethylcellulose, hydroxypropylmethylcellulose acetate succinate, hydroxypropylmethylcellulose phthalate, methacrylic acid copolymer L, methacrylic acid copolymer LD, dried methacrylic acid copolymer LD, methacrylic acid copolymer S, cellulose acetate phthalate, zein, and shellac;

14. the pharmaceutical composition in particle form cited in claim 1 or 2, where the middle layer comprises a heating-type insolubilizer and a heating-type insolubilizing substance;

15. the pharmaceutical composition in particle form cited in claim 14, where the heating-type insolubilizer is one or more selected from a group of substances with a ΔT of +3° C. or higher;

16. the pharmaceutical composition in particle form cited in claim 15, where the heating-type insolubilizer is one or more selected from the group consisting of magnesium chloride, ferric chloride, calcium chloride, magnesium sulfate, calcium oxide, sodium carbonate, calcium bromide, sodium acetate, copolyvidone, povidone, dibasic sodium phosphate, sodium polyphosphate, sodium pyrophosphate, and sodium hydroxide;

17. the pharmaceutical composition in particle form cited in any one of claims 14 through 16, where the heating-type insolubilizing substance is one or more selected from a group of substances with an $R_s$ of 0.8 or lower;

18. the pharmaceutical composition in particle form cited in any one of claims 14 through 16, where the heating-type insolubilizing substance is one or more selected from a group of substances having a $CST_3$ of 38° C. or higher but less than 45° C.;

19. the pharmaceutical composition in particle form cited in claim 17, where the heating-type insolubilizing substance is one or more selected from the group of substances consisting of calcium carbonate and magnesium carbonate;

20. the pharmaceutical composition in particle form cited in claim 18, where the heating-type insolubilizing substance is one or more selected from the group of substances consisting of polymers containing N-isopropylacrylamide and derivatives where hydrophobic groups have been introduced to the N position of acrylamide, polymers containing derivatives wherein a hydrophobic group has been introduced to position N of methacrylamide, polymers containing derivatives wherein a hydrophobic group has been introduced to position O of cellulose, polymers containing derivatives where a hydrophobic group has been introduced to position O of vinyl alcohol, polymers containing polypentapeptides, polymers containing amino acid derivatives, polymers containing polyalkylene oxide, polymers with nitrogen-containing cyclic groups, and poly(methylvinyl ether);

21. the pharmaceutical composition in particle form cited in claim 1 or 2, where the middle layer comprises a cooling-type insolubilizer and a cooling-type insolubilizing substance;

22. the pharmaceutical composition in particle form cited in claim 21, where the cooling-type insolubilizer is one or more selected from a group of substances with a ΔT of −3° C. or lower;

23. the pharmaceutical composition in particle form cited in claim 22, where the cooling-type insolubilizer is one or more selected from the group of substances consisting of ammonium chloride, ammonium nitrate, ammonium carbonate, urea, potassium chloride, disodium hydrogen phosphate dodecahydrate, potassium bicarbonate, disodium carbonate decahydrate, glycine, disodium thiosulfate pentahydrate, sodium bicarbonate, ammonium oxalate monohydrate, malic acid, disodium succinate hexahydrate, cysteine hydrochloride, succinic acid, and sodium acetate trihydrate;

24. the pharmaceutical composition in particle form cited in any one of claims 21 through 23, where the cooling-type insolubilizing substances is one or more selected from a group of substances having an $R_s$ of 1.4 or greater;

25. the pharmaceutical composition in particle form cited in any one of claims 21 through 23, where the cooling-type insolubilizing substance is one or more selected from a group of substances having a $CST_4$ of 28° C. or higher but less than 36° C.;

26. the pharmaceutical composition in particle form cited in claim 24, where the cooling-type insolubilizing substance is one or more selected from the group of substances consisting of sodium pyrophosphate, adipic acid, succinic acid, salicylic acid, and hydroquinone;

27. the pharmaceutical composition in particle form cited in claim 25, where the cooling-type insolubilizing substance is one or more selected from the group of substances consisting of copolymers of vinyl monomers having functional groups that function as proton donors (carboxyl groups, sulfone groups, styrenesulfone groups, and other groups) and vinyl monomers having functional groups that function as proton acceptors (amide group and other groups); mixtures of vinyl polymers having functional groups that function as proton donors (carboxyl group, sulfone group, styrenesulfone group, and other groups) and vinyl polymers having functional groups that function as proton acceptors (amide group and other groups); vinyl polymers having functional groups that function as proton donors and functional groups that function as proton acceptors (poly(N-acrylamide) and the like); copolymers of vinyl monomers having anionic functional groups and vinyl monomers having cationic functional groups; and mixtures of vinyl polymers having anionic functional groups and vinyl polymers having cationic functional groups; vinyl polymers having anionic functional groups and cationic functional groups;

28. the pharmaceutical composition in particle form cited in claim 25, where the cooling-type insolubilizing substance is one or more selected from a mixture of a salting out-type insolubilizer and one or more selected from the group of substances consisting of copolymers of vinyl monomers having functional groups that function as proton donors (carboxyl group, sulfone group, styrenesulfone group, and other groups) and vinyl monomers having functional groups that function as proton acceptors (amide group and other groups); mixtures of a vinyl polymers having functional groups that function as proton donors (carboxyl group, sulfone group, styrenesulfone group, and other groups) and vinyl polymers having functional groups that function as proton acceptors (amide groups and other groups); vinyl polymers having functional groups that function as proton donors and functional groups that function as proton acceptors (poly(N-acrylamide), and the like); copolymers of vinyl monomers having anionic functional groups and vinyl monomers having cationic functional groups; mixtures of vinyl polymers having anionic functional groups and vinyl polymers having cationic functional groups; and vinyl polymers having anionic functional groups and cationic functional groups;

29. the pharmaceutical composition in particle form cited in any one of claims 1 through 28, where the ratio of insolubilizer in terms of the weight of the middle layer is 20 wt % or greater but less than 95 wt %;

30. the pharmaceutical composition in particle form cited in any one of claims 1 through 29, where the amount of coating of the middle layer is 1 to 500 wt % per core particle containing drug;

31. the pharmaceutical composition in particle form cited in any one of claims 1 through 30, where the layer for controlling water penetration contains one or more water-insoluble substance and further, can contain one or more water-soluble substance;

32. the pharmaceutical composition in particle form cited in claim 31, where the water-insoluble substance is one or more selected from the group consisting of ethylcellulose, cellulose acetate, polyvinyl acetate, cellulose acetate phthalate, carboxymethylethylcellulose, hydroxypropylmethylcellulose acetate succinate, hydroxypropylmethylcellulose phthalate, dimethylpolysiloxane, polydimethylsiloxane-silicon dioxide mixture, dimethylaminoethylmethacrylate-methylmethacrylate copolymer, methylacrylate-methacrylic acid copolymer, ethyl acrylate-methyl methacrylate copolymer emulsion, aminoalkyl methacrylate copolymer RS, dried methacrylic acid copolymer LD, aminoalkyl methacrylate copolymer E, methacrylic acid copolymer L, methacrylic acid copolymer LD, methacrylic acid copolymer S, polyvinylacetal diethylaminoacetate, casein, shellac, and zein;

33. the pharmaceutical composition in particle form in claim 31 or 32, where the water-soluble substance is one or more selected from the group consisting of powdered acacia, sodium alginate, pregelatinized starch, sodium caseinate, carrageenan, carboxyvinyl polymer, sodium carboxymethyl starch, carmellose sodium, xanthan gum, sucrose esters of fatty acids, dextran, dextrin, lactose, hydroxypropylcellulose, hydroxypropylmethylcellulose, methylcellulose, hydroxyethylcellulose, pullulan, povidone, copolyvidone, polyoxyethylene hydrogenated castor oil, polyoxyethylene polyoxypropylene glycol, aminoalkyl methacrylate copolymer E, polyvinylacetal diethylaminoacetate, polyvinyl alcohol-polyethylene glycol graft copolymer, polyvinyl alcohol, macrogol, polyethylene oxide, glycine, alanine, aspartame, glycyrrhizinic acid, sucrose, fructose, maltose, glucose, cyclodextrin, mannitol, xylitol, maltitol, and sorbitol;

34. the pharmaceutical composition in particle form cited in any one of claims 1 through 33, where the drug contained in the particles is a drug that has an unpleasant taste;

35. the pharmaceutical composition in particle form cited in claim 34, where the drug contained in the particles is solifenacin or a salt thereof, or diphenhydramine or a salt thereof;

36. the pharmaceutical composition in particle form cited in any one of claims 1 through 35, where the average particle diameter of the pharmaceutical composition in particle form is 1 to 350 μm;

37. fast-disintegrating tablets, characterized in that they contain the pharmaceutical composition in particle form cited in any one of claims 1 through 36.

The "pharmaceutical composition in particle form" of the present invention means a composition of drug-containing particles that are smaller than the specific size described below and are administered in a variety of forms together with one or more pharmaceutical excipients. When the shape of the composition particles is approximately spherical, size of the pharmaceutical composition in particle form is set at an average particle diameter of 2 mm or smaller. Moreover, if the pharmaceutical composition in particle form is a shape other than spherical, the size of the pharmaceutical composition in particle form is set at an average major axis of 2 mm or smaller. According to the knowledge of the inventors, pharmaceutical preparations that are smaller than the sizes specified above pose objectives in that it is difficult to simultaneously (1) suppress initial drug release, (2) obtain fast drug release thereafter, and (3) control lag time.

According to the knowledge of the inventors, the meaning of the expression "suppress drug release for a specific time" is as follows. The "drug release is suppressed" or "initial drug release is suppressed" in the present invention is defined as a drug dissolution rate kept at 0 to 3% in dissolution tests using a test fluid that simulates the oral cavity. Masking the unpleasant taste of a drug, preventing oral absorption, and other objectives cannot be accomplished if in the above-mentioned dissolution tests a drug dissolution rate is not kept at 0 to 3%. Moreover, the time for which the drug dissolution rate is 0 to 3% is defined as the "lag time." According to the knowledge of the inventors, when a pharmaceutical composition in particle form is taken, a lag time of two minutes or longer is necessary in order to mask the unpleasant taste of a drug, prevent oral absorption, and the like. Furthermore, there is a demand for the capability to control the length of the lag time as needed by increasing or decreasing the amount of excipients in the composition, and other means taking into consideration the fact that the extent of the unpleasant taste, the time for which the taste remains, the speed of oral absorption, the time for which the pharmaceutical preparation is retained in the oral cavity, and the like vary with the properties and purpose of the drug or pharmaceutical preparation.

Moreover, according to the knowledge of the inventors, the definition of the expression "drug is quickly released" in the present invention is as follows. "The drug is quickly released" or "fast drug release" is defined as a drug dissolution rate one hour after starting the dissolution test of 90 to 100% in tests using test fluid that simulates gastrointestinal fluid. If the drug dissolution rate one hour after starting the test has not reached 90% in the above-mentioned dissolution test, there will be a reduction in upper gastrointestinal absorption of the drug and there will be no hope of realizing the fullest pharmacological effects.

The "unpleasant taste" in the present invention means a taste that is unpleasant when the drug is taken, specifically a bitter taste, a tart taste, an acrid taste, a sour taste, a hot taste, an astringent taste, and the like.

The "insolubilization" in the present invention indicates the phenomenon whereby solubility or the dissolution speed in water decreases, and "becomes insoluble", "causes to become insoluble", or "promotes insolubilization" indicates that separation from the aqueous phase, precipitation and sedimentation of a dissolved substance is promoted, or dissolution of a solid substance that has not yet dissolved in water is prevented.

Based on the knowledge that the pH inside the oral cavity is approximately 6.8, the "test fluid that simulates the inside of the oral cavity" in the present invention means a phosphate buffer with a pH of 6.8 (2nd fluid identified in Disintegration Test cited in The Japanese Pharmacopeia fourteenth edition, the same hereafter), and taking into consideration changes in stomach pH, the "testing fluid that simulates gastrointestinal fluid" is a hydrochloride buffer with a pH of 1.2 (1st fluid identified in Disintegration Test cited in The Japanese Pharmacopeia fourteenth edition, the same hereafter) or a phosphate buffer with a pH of 6.8.

The structure of the oral pharmaceutical composition in particle form of the present invention will now be described.

The "core particles containing a drug" in the present invention means particles composed of drug only, or particles composed of a drug and one or more excipients.

The "middle layer" of the present invention means a coating layer that is between the core particles containing a drug and the layer for controlling water penetration and that contains one or more insolubilizers and one or more insolubilizing substances. The core particles containing a drug can be directly coated with the middle layer. Moreover, the core particles containing a drug can be pre-coated with a component that will not prevent lag time formation or fast drug release thereafter as one or more coating layers and then coated with the middle layer. The middle layer contains two or more essential components (insolubilizer and insolubilizing substance), but the core particles can be coated with one layer that contains all of these plural essential components. These components can be uniform throughout one layer or they can be unevenly distributed throughout one layer. Moreover, it is also possible for the core particles to be coated by plural middle layers, with two or more essential components (insolubilizer and insolubilizing substance) divided into two or more layers, and in this case, the components can be divided in any manner and disposed in any manner. Even if there are plural layers, the coating layers containing plural essential components are together referred to as the middle layer.

The "layer for controlling water penetration" is a layer that contains one or more water-insoluble substances and optionally contains one or more water-soluble substance, and the core particles containing a drug that have been coated with the middle layer are further coated with this layer for controlling water penetration. The layer for controlling water penetration suppresses the dissolution speed of the middle layer and allows a lag time to form by controlling the speed with which water penetrates to the inside of the pharmaceutical composition in particle form. The middle layer can be directly coated with the layer for controlling water penetration. It is possible to pre-coat the middle layer with one or more coating layers components that will not prevent lag time formation or fast drug release thereafter and then coat these particles with a layer that controls water penetration. The layer for controlling water penetration can also be coated with one or more layers of components that will not prevent lag time formation or fast drug release thereafter. In addition, as long as the water penetration speed can be controlled, there can be one layer for controlling the amount of water penetration, or there can be two or more plural layers for controlling the amount of water penetration. Even if there are plural layers, these coating layers for controlling the water penetration speed are collectively referred to as the layer for controlling Water penetration.

The middle layer of the present invention will now be described.

The "insolubilizer" of the present invention is one of the essential components found in the middle layer for obtaining the desired drug dissolution profile and is a general name for a group of substances that are water-soluble and have the ability to promote insolubilization of the insolubilizing substance described later. That is, the insolubilizer is a substance that has solubility of very soluble, freely soluble, soluble, sparingly soluble, or slightly soluble according to the regulations and measurement methods for "solubilities" cited in The Japanese Pharmacopeia fourteenth edition and that has the specific property values cited and defined in detail hereafter. An insolubilizer that has been dissolved in water changes the environment around an insolubilizing substance and renders the insolubilizing substance insoluble. Insolubilization by salting out, exposure to an acid, heating, and cooling are examples of the theory of insolubilization and for convenience, these will be named by their theory and referred to as a salting out-type insolubilizer, acid-type insolubilizer, heating-type insolubilizer, and cooling-type insolubilizer. As defined hereafter in detail, the inventors ascertained that the insolubilizer must have certain property values in order to render the insolubilizing substance insoluble. However, these are only examples of the insolubilization theory and types of insolubilizer, and they should not be interpreted as restricting.

The "salting out-type insolubilizer" that is used in the present invention is one of the essential components contained in the middle layer in order to obtain the desired drug release profile and is a pharmaceutically acceptable substance that has a $\Delta CST_1$ (refer to definition given hereafter) of 10° C. or higher, preferably $\Delta CST_1$ of 20° C. or higher. Specific examples are sodium carbonate, potassium carbonate, monobasic sodium phosphate, dibasic potassium phosphate, dibasic sodium phosphate, sodium metaphosphate, trisodium phosphate, monobasic potassium phosphate, potassium bicarbonate, sodium bicarbonate, ammonium carbonate, sodium polyphosphate, sodium pyrophosphate, sodium chloride, potassium chloride, calcium chloride, magnesium chloride, sodium sulfate, sodium sulfite, sodium bisulfite, sodium hydroxide, sodium citrate, dibasic sodium citrate, monosodium glutamate, arginine glutamate, disodium succinate, calcium acetate, glycine, alanine, sorbitol, xylitol, inositol, sucrose, glucose, and fructose, as well as hydrides thereof. Preferred examples are sodium carbonate, monobasic sodium phosphate, dibasic sodium phosphate, sodium metaphosphate, trisodium phosphate, potassium bicarbonate, sodium bicarbonate, sodium polyphosphate, sodium pyrophosphate, sodium chloride, potassium chloride, sodium sulfate, sodium sulfite, sodium citrate, dibasic sodium citrate, monosodium glutamate, disodium succinate, glycine, alanine, sorbitol, xylitol, inositol, sucrose, glucose, and fructose, as well as hydrates thereof, and particularly preferred examples are sodium carbonate, monobasic sodium phosphate, dibasic sodium phosphate, sodium citrate, and dibasic sodium citrate, as well as hydrates thereof. One or a combination of two or more of these salting out-type insolubilizers can be used as needed.

The "$\Delta CST_1$" in the present invention is the property value that shows the ability of a salting out-type insolubilizer to render insoluble a salting out-type insolubilizing substance that originally is water-soluble, and is measured by the following "Testing Method 1." The procedure of Testing Method 1 will now be described. A 25° C. saturated aqueous solution of the substance that is a candidate for the salting out-type insolubilizer is prepared and then this saturated aqueous solution is diluted two-fold and brought to a temperature of 25° C. (hereafter ½ saturated concentration aqueous solution). On the other hand, 25 g of an 0.3 wt % aqueous solution of hydroxypropylmethylcellulose (Shin-Etsu Chemical Co., Ltd.; TC-5E) is brought to 25° C. Twenty-five grams of the ½ saturated concentration aqueous solution of the candidate substance is added dropwise by approximately 1 g at a time to 25 g of the 0.3 wt % aqueous solution of hydroxypropylmethylcellulose. Once dropwise addition is completed, temperature of the mixture is increased from 0° C. or 25° C. The temperature at which the transparent mixture is macroscopically observed to become turbid serves as $CST_1$. On the other hand, temperature of an aqueous 0.3 wt % solution of hydroxypropylmethylcellulose (Shin-Etsu Chemical Co., Ltd.; TC-5E) is raised from 25° C. and the temperature at which the transparent aqueous solution is observed macroscopically to become turbid is $CST_0$ (critical solution temperature; Kagaku Daijiten 9 (Kyoritsu Shuppan Publishers)); the difference between $CST_0$ and $CST_1$ is defined as $\Delta CST_1$ ($\Delta CST_1 = CST_0 - CST_1$). A substance showing a positive $\Delta CST_1$ of 10° C. or higher, preferably a positive $\Delta CST_1$ of 20° C. or higher, is defined as a "salting out-type insolubilizer" in the present invention. $\Delta CST_1$ is a value that quantitatively determines the degree to which the CST (critical solution temperature) of hydroxypropylmethylcellulose will decrease when a candidate substance is present. Therefore, the ability of the candidate substance to render hydroxypropylmethylcellulose insoluble increases with a larger positive $\Delta CST_1$. The inventors discovered that hydroxypropylmethylcellulose is a typical salting out-type insolubilizing substance and confirmed that a substance with a strong ability to render hydroxypropylmethylcellulose insoluble also has strong ability to render other salting out-type insolubilizing substances insoluble.

The "acid-type insolubilizer" used in the present invention is one of the essential components contained in the middle layer in order to obtain the desired drug release profile and is a substance that has a pH of 5.0 or less when measured by Testing Method 2 described hereafter. Specific examples are dibasic sodium citrate, monobasic sodium phosphate, citric acid, malic acid, and tartaric acid. One or a combination of two or more acid-type insolubilizers can be used as needed.

The "pH measured by Testing Method 2" of the present invention is the property value that shows the ability of the acid-type insolubilizer to render insoluble an acid-type insolubilizing substance that is originally water-soluble and is measured by the following "Testing Method 2." The procedure of Testing Method 2 will now be described. The substance that is a candidate for the insolubilizer is dissolved in a test fluid that simulates the oral cavity, which has been brought to a temperature of 25° C. and stirred, to form a saturated solution and pH of this solution is measured. A substance that shows a pH of 5.0 or less is defined as an "acid-type insolubilizer" in the present invention. pH is the value that quantitatively determines the degree to which an aqueous solution becomes acidic when the candidate substance is dissolved in water. Therefore, the ability of the candidate substance to change the ambient water to acidic when it is dissolved in the water and render an acid-type insolubilizing substance insoluble rises with a lower pH.

The "heating-type insolubilizer" used in the present invention is one of the essential components contained in the middle layer in order to obtain the desired drug release profile and is a pharmaceutically acceptable substance having a $\Delta T$ (defined hereafter) of +3° C. or greater. Specific examples are magnesium chloride, ferric chloride, calcium chloride, magnesium sulfate, calcium oxide, sodium carbonate, calcium bromide, sodium acetate, copolyvidone, povidone, dibasic sodium phosphate, sodium polyphosphate, sodium pyrophosphate, and sodium hydroxide. Preferred examples are magnesium chloride, calcium chloride, calcium oxide, sodium carbonate, copolyvidone, povidone, anhydrous dibasic sodium phosphate, sodium polyphosphate, sodium pyrophosphate, and sodium hydroxide. One or a combination of two or more heating-type insolubilizers can be used as needed.

The "cooling-type insolubilizer" used in the present invention is one of the essential components contained in the middle layer in order to obtain the desired drug release profile and is a pharmaceutically acceptable substance with a $\Delta T$ of $-3°$ C. or lower. Specific examples are ammonium chloride, ammonium nitrate, ammonium carbonate, urea, potassium chloride, disodium hydrogen phosphate dodecahydrate, potassium bicarbonate, disodium carbonate decahydrate, glycine, disodium thiosulfate pentahydrate, sodium bicarbonate, ammonium oxalate monohydrate, malic acid, disodium succinate hexahydrate, cysteine hydrochloride, succinic acid, and sodium acetate trihydrate. Moreover, one or a combination of two or more cooling-type insolubilizers can be used as needed.

The "$\Delta T$" in the present invention is the property value showing the ability of a heating-type insolubilizer, or a cooling-type insolubilizer, to render insoluble an originally water-soluble heating-type insolubilizing substance, or a cooling-type insolubilizing substance, and is measured by the following "Testing Method 3." The procedure of Testing Method 3 will now be described. Five grams of the substance that is a candidate for the insolubilizer are placed in 50 mL of water that have been brought to 25° C. and stirred. Then the water temperature is measured. The water temperature when there is the greatest change in temperature from 25° C. once the candidate substance has been introduced is made To and the difference from 25° C. is defined as $\Delta T$ ($\Delta T = T_1 - 25$). $\Delta T$ is the value that quantitatively determines the amount of heat generated, or the amount of heat absorbed, that is, the heat of dissolution (Kagaku Daijiten (Tokyo Kagaku Dojin)), when the water-soluble substance is dissolved in water. A substance having a positive $\Delta T$ of +3° C. or higher is defined as a "heating-type insolubilizer." The ability of the candidate substance to generate heat with dissolution, raise the ambient temperature, and render the heating-type insolubilizing substance insoluble increases as $\Delta T$ becomes a larger positive value. Moreover, a substance having a negative $\Delta T$ of $-3°$ C.

or lower is defined as a "cooling-type insolubilizer." The ability of the candidate substance to absorb heat with dissolution, lower the ambient temperature, and render the cooling-type insolubilizing substance insoluble increases as ΔT becomes a larger negative value.

The "insolubilizing substance" of the present invention is one of the essential components contained in the middle layer for obtaining the desired drug release profile and is a general name for a group of water-soluble substances whose insolubilization is promoted by the above-mentioned insolubilizer. That is, the insolubilizing substance is a substance having solubility in water of standard (A), (B) or (C) listed below and having property values defined in detail hereafter. The solubility standards are (A) substances having solubility of very soluble, freely soluble, soluble, sparingly soluble, or slightly soluble according to the regulations and measurement methods for "solubilities" cited in The Japanese Pharmacopeia fourteenth edition; (B) substances cited in The Japanese Pharmacopeia fourteenth edition as being very soluble in water, being freely soluble in water, being slightly soluble in water, 1.0 g of powder dissolving almost completely in 2.0 mL of water, being practically insoluble in water but dissolving in dilute hydrochloric acid with effervescence, being practically insoluble in water but dissolving in sodium hydroxide TS, being practically insoluble in water, forming a viscous liquid addition of water, or swelling in water and producing slightly turbid viscous solution; and (C) substances cited in the Japanese Pharmaceutical Excipients 1998 as being very soluble in water, being freely soluble in water, being soluble in water, being sparingly soluble in water, being slightly soluble in water, being practically insoluble in water but dissolving in dilute sodium hydroxide TS, being practically insoluble in water but dissolving in sodium hydroxide reagent TS, dispersing homogeneously in water and dissolving in dilute sodium hydroxide TS, being practically insoluble in water but the solubility is increased in the presence of carbon dioxide, gradually dissolving in water, producing a viscous liquid on the addition of water, gradually dissolving and becoming a viscous liquid on the addition of water, swelling and producing a clear or white-turbid viscous liquid on the dispersion in water, producing a clear viscous liquid on the addition of water and being warmed, or producing a clear viscous liquid on the addition of water and being heated. The insolubilizing substance is rendered insoluble and a lag time is formed as a result of the insolubilizer changing the surrounding environment. When all of the insolubilizer is released from the pharmaceutical composition in particle form and the environment surrounding the insolubilizing substance becomes similar to the environment of the gastrointestinal system, the insolubilizing substance returns to its original water solubility and is dissolved and released, and the drug is also quickly released. Insolubilization by salting out, exposure to an acid, heating, and cooling have been given as examples of insolubilization theories and for convenience, each insolubilizing substance is named by its theory as a salting out-type insolubilizing substance, an acid-type insolubilizing substance, a heating-type insolubilizing substance, or a cooling-type insolubilizing substance. The inventors ascertained that an insolubilizing substance must have specific property values in order to be rendered insoluble by the insolubilizer, as is cited and defined in detail hereafter. However, the insolubilization theories and types of insolubilizing substances given as examples are only examples that can be used in the present invention and should not be interpreted as restricting. There are no special restrictions to the viscosity of the insolubilizing substance as long as the selected substance has a viscosity appropriate for accomplishing the objectives of the present invention. Taking the risk that the pharmaceutical composition in particle form will form an aggregate during coating, viscosity of an aqueous 2 wt % solution of insolubilizing substance as measured by the Method II: Viscosity Measurement by Rotational Viscometer of the Japanese Pharmacopeia fourteenth edition is less than 25,000 mPa·s, further less than 10,000 mPa·s, preferably less than 4,000 mPa·s, particularly less than 400 mPa·s, ideally less than 100 mPa·s.

The "salting out-type insolubilizing substance" used in the present invention is one essential component contained in the middle layer in order to obtain the desired drug release profile, and is a pharmaceutically acceptable substance having a $CST_2$ of 55° C. or lower and a $CST_3$ of 37° C. or higher, preferably a $CST_2$ of 20° C. or lower and a $CST_3$ of 37° C. or higher. Specific examples are hydroxypropylmethylcellulose, hydroxypropylcellulose, methylcellulose, polyvinyl alcohol-polyethylene glycol graft copolymer, carboxyvinyl polymer, polyvinyl alcohol, polyethylene oxide, povidone, copolyvidone, polyoxyethylene hydrogenated castor oil, polymers containing N-isopropylacrylamide and derivatives where hydrophobic groups have been introduced to the N position of acrylamide, polyoxyethylene polyoxypropylene glycol, macrogol (molecular weight of 6000 or greater), hydroxyethylcellulose, and the like. Preferred examples are hydroxypropylmethylcellulose, hydroxpropylcellulose, methylcellulose, polyvinyl alcohol-polyethylene glycol graft copolymer, carboxyvinyl polymer, polyvinyl alcohol, polyethylene oxide, povidone, copolyvidone, polyoxyethylene hydrogenated castor oil, polymers containing N-isopropylacrylamide and derivatives where hydrophobic groups have been introduced to the N position of acrylamide, and polyoxyethylene polyoxypropylene glycol. Particularly preferred examples are hydroxypropylmethylcellulose, methylcellulose, polyvinyl alcohol-polyethylene glycol graft copolymer, and polymers containing N-isopropylacrylamide and derivatives where hydrophobic groups have been introduced to the N position of acrylamide. One or a combination of two or more salting out-type insolubilization substances can be used as needed. When a substance is used alone, a substance having a $CST_2$ of 55° C. or higher and/or a $CST_3$ of 37° C. or lower can be used, while when a mixture of two or more substances is used, a mixture having a $CST_2$ of 55° C. or lower and a $CST_3$ of 37° C. or higher, preferably a mixture having a $CST_2$ of 20° C. or lower and a $CST_3$ of 37° C. or higher, can be used. Specific examples are mixtures of polyacrylic acid, polyvinyl alcohol, or other polymers having molecular structures that function as proton donors and polyethylene oxide, hydroxypropylcellulose, hydroxypropylmethylcellulose, methylcellulose, or other polymers having molecular structures that function as proton acceptors. Moreover, one or a combination of two or more of these mixtures can be used as needed.

The "$CST_2$" in the present invention is the property value showing how easily the salting out-type insolubilizing substance is rendered insoluble by the salting out-type insolubilizer and is measured by the following "Testing Method 4". The procedure of Testing Method 4 will now be described. A 25° C. saturated aqueous solution of sodium carbonate (Kanto Kagaku) is prepared and this saturated aqueous solution is diluted two-fold and brought to a temperature of 25° C. (½ saturated concentration aqueous solution hereafter). On the other hand, 25 g of an aqueous 0.3 wt % solution of a substance that is a candidate for a salting out-type insolubilizing substance is brought to 25° C. Twenty-five grams of the ½ saturated concentration aqueous solution of sodium carbonate is added dropwise by approximately 1 g at a time to 25 g of the 0.3 wt % aqueous solution of the candidate substance.

Once dropwise addition is completed, temperature of the mixture is increased from 0° C. or 25° C. The temperature at which the transparent mixture is macroscopically observed to become turbid serves as $CST_2$. A $CST_2$ that is 55° C. or lower, preferably 20° C. or lower, is the first condition for showing that a substance is a "salting out-type insolubilizer" in the present invention. $CST_2$ is a value that quantitatively determines the extent to which the CST (critical solution temperature) of a candidate substance is reduced by sodium carbonate. Therefore, a candidate substance is more easily rendered insoluble by sodium carbonate as the $CST_2$ becomes smaller. The inventors discovered that sodium carbonate is a typical salting out-type insolubilizer, and confirmed that substances that are easily rendered insoluble by sodium carbonate are easily rendered insoluble by other salting out-type insolubilizers.

On the other hand, "$CST_3$" in the present invention is the property value showing how easily a salting out-type insolubilizing substance is dissolved when this salting out-type insolubilizing substance that has been rendered insoluble recovers the original water-solubility thereof once all of the salting out-type insolubilizer has been dissolved and released. This value is measured by the following "Testing Method 5." The procedure for Testing Method 5 will now be described. An aqueous 0.3 wt % solution of a substance that is a candidate for a salting out-type insolubilizing substance is heated from 0° C. or 25° C., and the temperature at which the transparent mixture is observed macroscopically to become turbid is $CST_3$. A $CST_3$ of 37° C. or higher is the second condition for a "salting out-type insolubilization substance" of the present invention. $CST_3$ is the CST (critical solution temperature) of the original salting out-type insolubilizing substance once all of the salting out-type insolubilizer has been dissolved and released. Therefore, when the $CST_3$ is 37° C. or lower, the salting out-type insolubilizing substance will not dissolve in water at body temperature. In short, the salting out-type insolubilizing substance must dissolve in order to realize fast drug release after a lag time; therefore, the $CST_3$ must be 37° C. or higher.

The "acid-type insolubilizing substance" used here is a substance that is one essential component contained in the middle layer for obtaining the desired drug release profile and is a pharmaceutically acceptable substance that will dissolve in a test fluid that simulates the oral cavity and will not dissolve in a test fluid at a pH of 5.0 or lower. Specific examples are carboxymethylethylcellulose, hydroxypropylmethylcellulose acetate succinate, hydroxypropylmethylcellulose phthalate, methacrylic acid copolymer L (for instance, Rohm GmbH; Eudragit L), methacrylic acid copolymer LD (for instance, Rohm GmbH; Eudragit L30D-55), dried methacrylic acid copolymer LD (for instance, Rohm GmbH; Eudragit L100-55), methacrylic acid copolymer S (for instance, Rohm GmbH; Eudragit S), cellulose acetate phthalate, zein, and shellac. Moreover, one or a combination of two or more acid insolubilizing substances can be used.

The "heating-type insolubilizing substance" used in the present invention is pharmaceutically acceptable and is one of the essential components contained in the middle layer for obtaining the desired drug release profile. It includes the following two substance groups, heating-type insolubilizing substances A and heating-type insolubilizing substances B. Heating-type insolubilizing substances A are a group of substances with an $R_s$ of 0.8 or lower. Specific examples are calcium carbonate and magnesium carbonate. Heating-type insolubilizing substances B are a groups of substances with a $CST_3$ of 38° C. or higher but less than 45° C. Heating-type insolubilizing substances B with a $CST_3$ within this range are rendered insoluble when a heating-type insolubilizer raises the ambient temperature, and when the heating-type insolubilizing substance is released, it dissolves at body temperature of 36 to 38° C. and the drug can be quickly released. Specific examples are polymers that contain N-isopropylacrylamide and other derivatives where hydrophobic groups have been introduced to the N position of acrylamide or methacrylamide; polymers containing derivatives where hydrophobic groups have been introduced to position O of cellulose; polymers containing derivatives where hydrophobic groups have been introduced to the O position of vinyl alcohol; polymers containing polypentapeptide; polymers containing N-acryloyl-L-proline or other amino acid derivatives; polymers containing a polyalkylene oxide; polymers having N-acryloylpiperidine and other nitrogen-containing cyclic groups; poly(methylvinyl ether), and the like. Polymers containing N-isopropylacrylamide and derivatives where hydrophobic groups have been introduced to the N position of acrylamide are preferred. It is widely known that the hydrophilic-hydrophobic balance of a polymer can be changed and the $CST_3$ can be easily controlled by changing the type and amount of groups introduced to the N and O positions of polymers that contain derivatives wherein a substitution group has been introduced to acrylamide, methacrylamide, cellulose, amino acids, and the like, as cited in *Macromolecular Chemistry and Physics*, 202, 276-286 (2001), Chemical Communications, 106-107 (2003), and other references. There are no restrictions to the structure of the main chain that is introduced or the type or amount of groups that are introduced as long as the $CST_3$ of heating-type insolubilizing substance B of the present invention is 38° C. or higher but less than 45° C. It is widely known that the $CST_3$ can be controlled as needed by changing the type of amino acids in elastin and polypentapeptides with a repeating sequence of valine-proline-glycine-valine-glycine derived from elastin, as cited in *Angewandte Chemie International Edition*, 32, 819-841 (1993), and other references. There are no special restrictions to the type and sequence of the amino acids in heating-type insolubilizing substance B of the present invention as long as the $CST_3$ is 38° C. or higher but less than 45° C. Moreover, it is widely known that the $CST_3$ can be controlled as needed by forming a copolymer and/or crosslinking from the above-mentioned derivatives or a pentapeptide, polyalkylene oxide, and the like and another molecule, as cited in *Macromolecules*, 26, 2496-2500 (1993), and other references. There are no special restrictions to the polymer composition, or type of molecule that is made into a copolymer and/or crosslinked with structural units and the derivative cited as examples above, as long as the $CST_3$ of the heating-type insolubilizing substance B of the present invention is 38° C. or higher but less than 45° C. Moreover, it is widely known that the $CST_3$ can be controlled as needed by mixing polymers that have molecular structures that function as proton donors (polyacrylic acid, polyvinyl alcohol, and the like) and polymers that have molecular structures that function as proton acceptors (polyethylene oxide or hydroxypropylcellulose, hydroxypropylmethylcellulose, methylcellulose, and the like), as cited in *Macromlecules*, 35, 9164-9168 (2002), and other references. There are no restrictions to the structure of the polymer that is mixed and the mixture ratio of heating-type insolubilizing substance B of the present invention as long as the $CST_3$ is 38° C. or higher but less than 45° C. Moreover, one or a combination of two or more selected from heating-type insolubilizing substances A and/or heating-type insolubilizing substances B can be used for the heating-type insolubilizing substance as needed.

The "cooling-type insolubilizing substance" used in the present invention is pharmaceutically acceptable, is one essential component contained in the middle layer for obtaining the desired drug release pattern, and includes the following two groups; cooling-type insolubilizing substances A and cooling-type insolubilizing substances B. Cooling-type insolubilizing substances A is a group of substances with an $R_S$ of 1.4 or greater. Specific examples are sodium pyrophosphate, adipic acid, succinic acid, salicylic acid, and hydroquinone. Cooling-type insolubilizing substance B is a group of substances having a $CST_4$ of 28° C. or higher but less than 36° C. Specific examples are copolymers of vinyl monomers having functional groups that function as proton donors (carboxyl groups, sulfone groups, styrenesulfone groups, and the like) and vinyl monomers having functional groups that function as proton acceptors (amide groups, and the like); mixtures of vinyl polymers having functional groups that function as proton donors (carboxyl groups, sulfone groups, styrenesulfone groups, and the like) and vinyl polymers having functional groups that function as proton acceptors (amide groups, and the like); vinyl polymers having functional groups that function as proton donors and functional groups that function as proton acceptors (poly(N-acrylamide), and the like); copolymers of vinyl monomers having anionic functional groups and vinyl monomers having cationic functional groups; mixtures of vinyl polymers having anionic functional groups and vinyl polymers having cationic functional groups; and vinyl polymers having anionic functional groups and cationic functional groups. Functional groups (carboxyl groups, sulfone groups, and the like) having a structure wherein a hydrogen atom is bonded to an atom with a high electronegativity (fluorine atoms, oxygen atoms, nitrogen atoms, and the like) are known as the proton donors in the above-mentioned copolymers and polymer mixtures. Moreover, atoms with a high electronegativity that do not have a positive charge (fluorine atoms, oxygen atoms, nitrogen atoms, and the like) are generally known as proton acceptors. There are no restrictions to the structure of the proton donors and proton acceptors in the copolymers or polymer mixtures as long as $CST_4$ is 28° C. or higher but less than 36° C. It is known that $CST_4$ of the above-mentioned polymers, copolymers, and mixtures can be controlled as needed by mixing these polymers, copolymers, and mixtures with a salting out-type insolubilizer, but there are no restrictions to the type or amount of salting out-type insolubilizer that is mixed as long as $CST_4$ is 28° C. or higher but less than 36° C. Moreover, it is known that the $CST_4$ of the above-mentioned copolymers can be controlled as needed by changing polymer composition, but there are no restrictions to the copolymer composition as long as $CST_4$ is 28° C. or higher but less than 36° C. Moreover, the $CST_4$ of the above-mentioned mixture can be controlled as needed by changing the mixture ratio, but there are no restrictions to the mixture ratio as long as $CST_4$ is 28° C. or higher but less than 36° C.

The "$R_S$" in the present invention is the property value that shows how easily heating-type insolubilizing substance A, or cooling-type insolubilizing substance A, is rendered insoluble by a heating-type insolubilizer or cooling-type insolubilizer, and is measured by the following "Testing Method 6." The procedure of Testing Method 6 will be now described. A saturated aqueous solution of a substance that is a candidate for insolubilizing substances is prepared at 30° C. and 40° C. and solubility at 30° C. and 40° C. is measured by the dry weight method. The value obtained by dividing solubility at 40° C. by solubility at 30° C. serves as $R_S$ ($R_S$=(solubility at 40° C.)/(solubility at 30° C.)). A substance with an $R_S$ of 0.8 or less is defined as a "heating-type insolubilizing substance A" in the present invention. $R_S$ is the value that shows temperature dependency of the solubility of a candidate substance. As $R_S$ becomes a low value of 1.0 or less, there is a reduction in solubility with an increase in temperature and the candidate substance therefore is more easily rendered insoluble with heating by a heating-type insolubilizer. Moreover, a substance with an $R_S$ of 1.4 or greater is defined as a "cooling-type insolubilizing substance A" in the present invention. As $R_S$ becomes a high value of 1.0 or greater, there is a reduction in solubility with a reduction in temperature and the candidate substance can therefore be more easily rendered insoluble with cooling by a cooling-type insolubilizer.

The "$CST_4$" in the present invention is the property value that shows how easily a cooling-type insolubilizing substance B is rendered insoluble by cooling-type insolubilizer, and is measured by the following "Testing Method 7." The procedure of Testing Method 7 is described below. An aqueous 0.3 wt % solution of a substances that is a candidate for cooling-type insolubilizing substance B is reduced in temperature from 50° C. and the temperature at which the transparent mixture is macroscopically noted to become cloudy is $CST_4$. A substance showing a $CST_4$ of 28° C. or higher but less than 36° C. is defined as a "cooling-type insolubilizing substance B." A substance with a $CST_4$ within this range is rendered insoluble when a cooling-type insolubilizer changes the ambient temperature and once the cooling-type insolubilizing substance has been released, it is dissolved at body temperature of 36 to 38° C. and the drug can be quickly released.

There are no special restrictions to the ratio of insolubizer in terms of the weight of the middle layer as long as a ratio appropriate for accomplishing the objective of the present invention is selected. The ratio is 20 wt % or greater but less than 95 wt %, further 30 wt % or greater but less than 90 wt %, preferably 31 wt % or greater but less than 90 wt %, particularly 35 wt % or greater but less than 90 wt %, ideally 40 wt % or greater but less than 80 wt %

The amount of coating with the middle layer appropriate for realizing the objectives of the present invention is selected from 1 to 500 wt % per core particles containing the drug. The amount of coating is 1 to 306 wt %, further 20 to 200 wt %, preferably 25 to 200 wt %, particularly 30 to 200 wt %, ideally 30 to 100 wt %. If the amount of coating is less than 1 wt %, there is a chance that lag time will not be long enough. Taking efficiency and productivity into consideration, production time will be prolonged and production will become inefficient if there is too much coating. Moreover, there are no special restrictions to the ratio of middle layer in terms of the weight of the entire composition in particle form as long as it is a ratio appropriate for accomplishing the objective of the present invention is selected. The ratio is 0.1 to 95 wt %, preferably 1 to 85 wt %, further 3 to 80 wt %, particularly 5 to 70 wt %, ideally 10 to 60 wt %.

The layer for controlling water penetration will now be explained.

The "water-insoluble substance" in the layer for controlling water penetration of the present invention is one of the essential components contained in the layer for controlling water penetration that is intended to control the speed of water penetration and there are no special restrictions to this substance as long as it is a pharmaceutically acceptable substance having solubility in water satisfying any of the standards in (A), (B), (C) or (D) listed below. These standards are (A) substances having solubility of slightly soluble, very slightly soluble, or practically insoluble or insoluble according to the regulations and measurement methods for "solubilities" cited in The Japanese Pharmacopeia fourteenth edition; (B) substances cited as being practically insoluble in water, slightly soluble in water, or 1-g portion dissolving gradually in 20 mL of water in The Japanese Pharmacopeia fourteenth edition; (C) substances cited as being very slightly soluble in water, practically insoluble in water, dispersing homogeneously in water, or being slightly soluble in water in the Japanese Pharmaceutical Excipients 1998; and (D) substances cited as being practically insoluble in water in The Japanese Pharmaceutical Codex 1997. Specific examples are ethylcellulose (for instance, FMC; Aquacoat), cellulose acetate, polyvinyl acetate, cellulose acetate phthalate, carboxymethylethylcellulose, hydroxypropylmethylcellulose acetate succinate, hydroxypropylmethylcellulose phthalate, crospovidone, dimethylpolysiloxane, polydimethylsiloxane-silicone dioxide mixture, dimethylaminoethylmethacrylate-methylmethacrylate copolymer, methylacrylate-methacrylic acid copolymer, ethyl acrylate-methyl methacrylate copolymer emulsion (for instance Rohm GmbH; Eudragit NE30D), aminoalkylmethacrylate copolymer RS (for instance, Rohm GribH; Eudragit RS, Eudragit RL), dried methacrylic acid copolymer LD (for instance, Rohm GmbH; Eudragit L100-55), aminoalkyl methacrylate copolymer E (for instance, Rohm GmbH; Eudragit E), methacrylic acid copolymer L (for instance, Rohm GmbH; Eudragit L), methacrylic acid copolymer LD (for instance, Rohm GmbH; Eudragit L30D-55), methacrylic acid copolymer S (for instance, Rohm GmbH; Eudragit S), polyvinylacetal diethylaminoacetate, dried milky liquid white lac, casein, shellac, zein, microcrystalline cellulose, potato starch, aspartame, stearic acid and other higher fatty acids, cetanol, stearyl alcohol, and other higher fatty alcohols, carnauba wax, beeswax, paraffin, and other low-melting-point substances with a melting point of 30 to 120° C., sucrose esters of fatty acids and other esters of higher fatty acid and polyhydric alcohols, magnesium stearate, calcium stearate, and other higher fatty acid metal salts, fats obtained by adding hydrogen to castor wax and other oils, synthetic waxes, ferric oxide, titanium oxide and other metal oxides, light anhydrous silicic acid and other silicon dioxides, talc, kaolin, calcium silicate, and other mineral silicates, calcium carbonate, calcium phosphate, gypsum, and other insoluble calcium salts, magnesium carbonate, and aluminum hydroxide. Preferred examples are ethylcellulose (for instance, FMC; Aquacoat), cellulose acetate, polyvinyl acetate, cellulose acetate phthalate, carboxymethylethylcellulose, hydroxypropylmethylcellulose acetate succinate, hydroxypropylmethylcellulose phthalate, dimethylpolysiloxane, polydimethylsiloxane-silicone dioxide mixture, dimethylaminoethylmethacrylate-methylmethacrylate copolymer, methylacrylate-methacrylic acid copolymer, ethyl acrylate-methyl methacrylate copolymer emulsion (for instance Rohm GmbH; Eudragit NE30D), aminoalkylmethacrylate copolymer RS. (for instance, Rohm GmbH; Eudragit RS, Eudragit RL), dried methacrylic acid copolymer LD (for instance, Rohm GmbH; Eudragit L100-55), aminoalkyl methacrylate copolymer E (for instance, Rohm GmbH; Eudragit E), methacrylic acid copolymer L (for instance, Rohm GmbH; Eudragit L), methacrylic acid copolymer LD (for instance, Rohm GmbH; Eudragit L30D-55), methacrylic acid copolymer S (for instance, Rohm GmbH; Eudragit S), polyvinylacetal diethylaminoacetate, casein, shellac, and zein. Moreover, one or a combination of two or more of these water-insoluble substances can be used as needed.

The "water-soluble substance" in the layer for controlling water penetration of the present invention is a pharmaceutically acceptable component that can be contained in the layer for controlling water penetration together with water-insoluble substance in order to control the water penetration speed, and is a substance having the solubility in water by any of standards (A), (B), and (C) below. These standards of "solubilities" are (A) a substance cited in The Japanese Pharmacopeia fourteenth edition as having solubility of very soluble, freely soluble, soluble or sparingly soluble; (B) a substance cited in The Japanese Pharmacopeia fourteenth edition as being very soluble in water, being freely soluble in water, being soluble in water, 1.0 g of powder dissolving almost completely in 2.0 mL of water, forming a viscous liquid addition of water, or swelling in water and producing a clear or slightly turbid viscous solution; and (C) a substance cited in the Japanese Pharmaceutical Excipients 1998 as being very soluble in water, freely soluble in water, soluble in water, sparingly soluble in water, dissolving gradually in water, producing a viscous liquid on the addition of water, swelling and becoming a white-turbid liquid on the addition of water, gradually dissolving and becoming a viscous liquid on the addition of water, swelling and becoming a viscous and pasty liquid on the addition of water, producing a clear viscous liquid on the addition of water and being warmed, producing a clear viscous liquid on the addition of water and being heated, or swelling and producing a clear or white-turbid viscous liquid on the dispersion in water. Specific examples of water-soluble substances contained in the layer for controlling water penetration of the present invention are powdered acacia, sodium alginate, pregelatinized starch, sodium caseinase, carrageenan, carboxyvinyl polymer, sodium carboxymethyl starch, carmellose sodium, xanthan gum, sucrose esters of fatty acids, dextran, dextrin, lactose, hydroxypropylcellulose, hydroxypropylmethylcellulose, methylcellulose, hydroxyethylcellulose, pullulan, povidone, copolyvidone, polyoxyethylene polyoxypropylene glycol, aminoalkyl methacrylate copolymer E (for instance, Rohm GmbH; Eudragit E), polyvinylacetal diethylaminoacetate, polyvinyl alcohol-polyethylene glycol graft copolymer, polyvinyl alcohol, macrogol, polyethylene oxide, glycine, alanine, and other amino acids, glycyrrhizinic acid and other sweeteners, sucrose, fructose, maltose, glucose, cyclodextrin and other sugars, and mannitol, xylitol, maltitol, sorbitol, and other sugar alcohols. Preferred examples are powdered acacia, sodium alginate, pregelatinized starch, sodium caseinase, carrageenan, carboxyvinyl polymer, sodium carboxymethyl starch, carmellose sodium, xanthan gum, dextran, dextrin, lactose, hydroxypropylcellulose, hydroxypropylmethylcellulose, methylcellulose, hydroxyethylcellulose, pullulan, povidone, copolyvidone, polyoxyethylene, hydrogenated castor oil, polyoxyethylene polyoxypropylene glycol, aminoalkyl methacrylate copolymer E (for instance, Rohm GmbH; Eudragit E), polyvinylacetal diethylaminoacetate, polyvinyl alcohol-polyethylene glycol graft copolymer, polyvinyl alcohol, macrogol, and polyethylene oxide. One or a combination of two or more of the water-soluble substances can be used as needed.

The composition ratio of water-insoluble substance and water-soluble substance in the layer for controlling water penetration of the present invention is the ratio appropriate for achieving the purpose of the present invention in accordance with drug properties, stability, site of absorption, and type of preparation and purpose of use. Specifically, the ratio of water-insoluble substance in the layer for controlling water penetration is 20 to 100 wt %, preferably 30 to 100 wt %, particularly 60 to 100 wt %, ideally 70 to 100 wt %. If the ratio of water-insoluble substance is less than 20 wt %, there is a chance that it will not be possible to sufficiently control the speed with which water penetrates to inside the pharmaceutical composition in particle form and that a sufficiently long lag time cannot be formed.

The amount appropriate for accomplishing the purpose of the present invention is selected as the amount of coating of the layer for controlling water penetration in the present invention, and is 0.1 to 150 wt % per core particles containing a drug. The preferred amount of coating is 0.5 to 150 wt %, further 1 to 100 wt %, particularly 2 to 50 wt %, ideally 3 to 40 wt %. If the amount of coating is less than 0.1 wt %, the coating will not be uniform over the surface of the pharmaceutical composition in particle form and thickness of the layer for controlling water penetration will be extremely thin; therefore, it will not be possible to sufficiently control the speed with which water penetrates the pharmaceutical composition in particle form and it is impossible to form a lag time that is long enough. If there is too much coating, quick drug release after the lag time will not be realized.

There are no special restrictions to the drug used in the present invention as long as it is an active ingredient that is effective in terms of treatment or an active ingredient that is effective in terms of prevention. Examples of this pharmaceutically active ingredient are hypnotic sedatives, sleep-inducing agents, migraine drugs, anti-anxiety drugs, anti-epilepsy drugs, antidepressants, anti-Parkinson's drugs, psychoneurotic drugs, central nervous system drugs, local anesthetics, skeletal muscle relaxants, autonomic nerve drugs, antipyretic analgesic anti-inflammatory agents, antispasmodics, anti-vertigo drugs, cardiotonics, drugs for arrhythmia, diuretics, hypotensives, vasoconstrictors, vasodilators, drugs for the circulatory system, drugs for hyperlipidemia, drugs to promote respiration, antitussives, expectorants, antitussive expectorants, bronchodilators, antidiarrheal agents, drugs for controlling intestinal function, drugs for peptic ulcer, stomachics, antacids, laxatives, cholagogues, gastrointestinal drugs, adrenocortical hormones, hormones, urogenital drugs, vitamins, hemostatics, drugs for liver disease, drugs used for gout, drugs used for diabetes, antihistamines, antibiotics, antibacterials, drugs used against malignant tumors, chemotherapeutic drugs, multisymptom cold medications, nutrition-enhancing health drugs, and osteoporosis drugs. Examples of these drugs are drugs used to treat an overactive bladder, such as solifenacin and tolterodine, sleep-inducing drugs, such as diphenhydramine and lorazepam, anti-inflammatory, antipyretic antispasmodics or analgesics, such as indomethacin, diclofenac, diclofenac sodium, codeine, ibuprofen, phenylbutazone, oxyfenbutazone, mepirizole, aspirin, etenzamide, acetaminophen, aminopyrine, phenacetin, butyl scopolamine bromide, morphine, etomidoline, pentazocine, fenoprofen calcium, naproxen, celecoxib, vardecoxib, tramadole, migraine drugs, such as sumatriptan, anti-rheumatic drugs, such as etodolac, anti-tuberculosis drugs, such as isoniazide, ethambutol chloride, drugs for the circulatory system, such as isosorbid nitrate, nitroglycerin, nifedipine, bardnidipine hydrochloride, nicardipine hydrochloride, dipyridamole, anrinone, indenolol hydrochloride, hydralazine hydrochloride, methyldopa, fuirosemide, spironolactone, guanetidine nitrate, resperine, amosulalol hydrochloride, lisinopril, methoprolol, pilocarpine, telmisartan, psychoneurotic drugs, such as chlorpromazine hydrochloride, amitriptyline hydrochloride, nemonapride, haloperidol, moperone hydrochloride, perphenazine, diazepam, lorazepam, chlordiazepoxide, adinazolam, alprazolam, methylphenidate, milnasivran, peroxetin, risperidone, sodium valproate, antidepressants, such as imipramine, antiemetics, such as methoclopramide, ramosetron hydrochloride, granisetron hydrochloride, ondansetron hydrochloride, azasetron hydrochloride, antihistamines, such as chlorpheniramine maleate, vitamins, such as thiamine nitrate, tocopherol acetate, sicotiamine, pyridoxal phosphate, cobamamide, ascorbic acid, nicotinamide, anti-gout drugs, such as allopurinol, colchicine, probenamide, anti-Parkinson's drugs, such as levodopa, selegiline, etc., hypnotic sedatives, such as amobarbital, bromwarelyl urea, midazolam, chloral hydrate, etc., anti-malignant tumor drugs, such as fluorouracil, carmofuir, aclarubicin hydrochloride, cyclophosphamide, thiotepa, anti-allergy drugs, such as pseudoephedrine, terfenadine, decongestants, such as phenyl propanolamine, ephedrines, drugs used to treat diabetes, such acethexamide, insulin, torbutamide, desmopressine, glibizide, and nateglinide, diuretics, such as hydrochlorthiazide, polythiazide, triaterene, bronchodilators, such as aminophylline, formoterol fumarate, theophylline, antitussives, such as codeine phosphate, noscapine, dimemorphan phosphate, dextromethorphan, antiarrythmia drugs, such as quinidine nitrate, digitoxin, propafenone hydrochloride, procainamide, surface anesthetics, such as aminoethyl benzoate, lidocaine, dibucaine hydrochloride, antiepilepsy drugs, such as phenytoin, etosuccimide, primidone, synthetic corticosteroids, such as hydrocortisone, prednisolone, triamcinolone, betamethasone, drugs for the digestive tract, such as famotidine, ranitidine hydrochloride, cimetidine, sucralfate, sulpiride, tepronone, praunotol, 5-aminosalicylic acid, sulfasalazine, omeprazole, lansoprazole, drugs for the central nervous system, such as indeloxazine, idebenone, thiapride hydrochloride, bifermerane hydrochloride, calcium homopanthothenate, agents for treatment of hyperlipidemia, such as pravastatin sodium, sinvastatin, lovastatin, atorvastatin, antibiotics, such as ampicillin phthalizyl hydrochloride, cefotetan, josamycin, BPH therapeutic agents, such as tamsulosin, doxazocin mesilate, terazosine hydrochloride, anti-asthma drugs, such as pranlukast, zafirlukast, albuterol, ambroxole, budesonide, leverbuterol, prostaglandin $I_2$ derivative agents for improving peripheral circulation, such as velaprost sodium, agents for treatment of various complications of diabetes, agents for treatment of skin ulcers, and the like. The drug can be used in free form or as any salt that is pharmaceutically acceptable. Moreover, one or a combination of two or more drugs can be used. These drug are examples of those that can be used in the present invention and should not be interpreted as restricting. The drugs contained in the pharmaceutical composition in particle form of the present invention is particularly a drug that requires timed-release, a drug that requires fast dissolution after lag time, particularly an unpleasant tasting drug or a drug that poses problems such as adverse events or individual differences in pharmacological effects with absorption in the oral cavity. Drugs that have an unpleasant taste and the like are well known and examples are drugs cited as drugs having a bitter taste in International Patent Application Early Disclosure (WO)02/02083. However, drugs with an unpleasant taste are not limited to these examples. Examples of drugs with an unpleasant taste are drugs having a bitter or astringent taste, such as solifenacin and salts thereof and diphenhydramine and salts thereof.

The amount of drug in the pharmaceutical composition in particle form of the present invention is selected as needed based on the type of drug at its medical use (indications), but there are no particular restrictions as long as it is the amount that is effective in terms of treatment or the amount that is effective in terms of prevention. The preferred amount of drug is 0.5 to 90 wt %, particularly 0.5 to 80 wt %, ideally 0.5 to 70 wt %, in terms of the entire pharmaceutical composition in particle form. However, the amounts of drug listed here are only examples of the amount that can be used in the present invention and should not be interpreted as being restricting.

There are no particular restrictions to the particle diameter of the pharmaceutical composition in particle form of the present invention as long as it is a major axis of 2 mm or smaller. There are no particularly restrictions to the particle diameter of the pharmaceutical composition in particle form when it is contained in fast-disintegrating tablets as long as there is not an uncomfortable gritty sensation when the tablets are taken. The average particle diameter is preferably adjusted to 350 μm or smaller. The particularly preferred average particle diameter is 1 to 350 μm, and the ideal average particle diameter is 20 to 350 μm.

Conventional methods commonly used in the present field can be employed for the pharmaceutical composition in particle form of the present invention, and there are no particular restrictions to the pharmaceutical additives other than the essential components as long as they are pharmaceutically acceptable and generally used as additives. Examples of these additives are binders, disintegrating agents, lubricants, flavoring agents, sweeteners, refrigerants, flavors and spices, fragrances, coloring agents, foaming agents, stabilizers, antioxidants, preservatives, pH regulators, solubilizers, dissolution auxiliary agents, fluidizers, buffers, bases, fillers, and the like, but these additives are not limited to these examples.

The pharmaceutical composition in particle form of the present invention can be made into a variety of forms of pharmaceutical compositions for oral administration together with one or more pharmaceutical additives. Examples of this form of pharmaceutical composition for oral administration are fast-disintegrating tablets, tablets, capsules, powders, granules, pills, troches, and dry syrups, but the pharmaceutical composition for oral administration is not limited to these forms.

The fast-disintegrating tablets containing pharmaceutical composition in particle form of the present invention will now be described.

The "fast-disintegrating tablet" of the present invention means a tablet or another pharmaceutical form similar to a tablet that is disintegrated by virtually only the saliva in the oral cavity within two minutes, preferably within one minute, particularly within 30 seconds, when the tablet is taken without water.

The pharmaceutical composition in particle form of the present invention can be contained in this type of fast-disintegrating tablet, and a fast-disintegrating tablet can be made using this pharmaceutical composition in particle form as the drug for the fast-disintegrating tablets, the fast-disintegrating tablet bases, and the methods cited in, for instance, International Publication 95-20380 (corresponding U.S. Pat. No. 5,576,014 Specification), International Publication 2002-92057 (corresponding U.S. patent application Early Disclosure 2003/099701 Specification), U.S. Pat. No. 4,305,502 Specification, U.S. Pat. No. 4,371,516 Specification, U.S. Pat. No. 2,807,346 (corresponding U.S. Pat. No. 5,466,464 Specification), JP (Kokai) H5-271054 (corresponding EP 553777 Specification), JP (Kokai) H10-182436 (corresponding U.S. Pat. No. 5,958,453 Specification), U.S. Pat. No. 3,412,694 (corresponding U.S. Pat. No. 5,223,264 Specification), and International Publication Pamphlet WO98/02185 (corresponding U.S. Pat. No. 6,287,596 Specification). Examples of fast-disintegrating tablets containing a pharmaceutical composition in particle form are fast-disintegrating tablets cited in U.S. Pat. No. 3,412,694 (corresponding U.S. Pat. No. 5,223,264 Specification) and JP (Kokai) 2003-55197. These fast-disintegrating tablets can contain the pharmaceutical composition in particle form of the present invention.

The fast-disintegrating tablets given as examples above are generally classified into molded type, wet-method type, and conventional tableted type, and the pharmaceutical composition in particle form of the present invention can be contained in any of these types of fast-disintegrating tablets. Molded tablets that disintegrate quickly in the oral cavity are made by filling and drying a solution or suspension of filler, and the like in a mold, as disclosed in U.S. Pat. No. 2,807,346 (corresponding U.S. Pat. No. 5,466,464 Specification). Molded type tablets that disintegrate quickly in the buccal cavity comprising the pharmaceutical composition in particle form of the present invention can be made by, for instance, filling a solution or suspension of the pharmaceutical composition in particle form of the present invention, a filler such as a saccharide, and a binder such as gelatin or agar in a PTP pocket and then removing the moisture by a method such as freeze drying, drying under reduced pressure, or low-temperature drying. Wet method-type tablets that disintegrate quickly in the buccal cavity are made by moistening a filler such as a saccharide, tableting under low pressure, and then drying, as disclosed in U.S. Pat. No. 3,069,458 (corresponding U.S. Pat. No. 5,501,861 Specification, corresponding U.S. Pat. No. 5,720,974, Specification). Wet-method type tablets that disintegrate quickly in the buccal cavity comprising the pharmaceutical composition in particle form of the present invention are prepared by, for instance, moistening the pharmaceutical compostion in particle form of the present invention and a filler such as a saccharide with a small amount of water or a mixture of water and alcohol, tableting this moistened mixture under low pressure, and then drying.

Ordinary tablet type tablets are prepared through conventional tableting processes as disclosed in International Publication 95-20380 (corresponding U.S. Pat. No. 5,576,014 Specification), International Publication 2002-92057 (corresponding U.S. patent application Early Disclosure 2003/099701 Specification), JP (Kokai) H10-182436 (corresponding U.S. Pat. No. 5,958,453 Specification), JP (Kokai) H9-48726, JP (Kokai) H8-19589 (corresponding U.S. Pat. No. 5,672,364 Specification), U.S. Pat. No. 2,919,771, and U.S. Pat. No. 3,069,458 (corresponding U.S. Pat. No. 5,501,861 Specification, corresponding U.S. Pat. No. 5,720,974 Specification). When preparing the ordinary tablet type of fast-disintegrating tablets containing the pharmaceutical composition of the present invention are prepared, for instance, it is possible to make fast-disintegrating tablets by granulating the pharmaceutical composition in particle form of the present invention and a filler, such as a saccharide of low moldability, using a solution or suspension of a saccharide of high moldability or a water-soluble polymer, and then comprerssion molding this granulated product to make a compressed product, and optionally humidifying and drying this compressed product, as disclosed in International Publication 95-20380 (corresponding U.S. Pat. No. 5,576,014 Specificaiton) and U.S. Pat. No. 2,919,771. When preparing the ordinary tablet type of fast-disintegrating tablets as disclosed in International Publication 99-47124 (corresponding U.S. Pat. No. 6,589,554 Specification), it is possible to produce fast-disintegrating tablets by, for instance, compressing of the pharmaceutical composition in particle form of the present invention, a filler such as crystalline saccharide, and the like using an amorphous saccharide, and then performing humidification and drying. Furthermore, when preparing ordinary tablet type of fast-disintegrating tablets such as disclosed in International Publication 2002-92057 (corresponding U.S. patent application Early Disclosure 2003/099701 Specification), it is possible to prepare fast-disintegrating tablets by compressing a mixture of the pharmaceutical composition in particle form of the present invention, filler, and a saccharide with a lower melting point than this filler, heating the compressed product, melting and then solidifying a saccharide with a low melting point for crosslinking. Tablet strength of the fast-disintegrating tablet can be increased by this type of humidification and drying or heat treatment.

A conventional filler can be used as the filler for the fast-disintegrating tablets of the present invention, but it is particularly preferred that a pharmaceutically acceptable saccharide be used. A saccharide of low moldability can be used for technology that employs the moldability of a saccharide; a crystalline saccharide can be used for technology that increases tablet strength with the crystalline and amorphous nature of a saccharide and humidification and drying; and in addition to a conventional filler, a saccharide with a high melting point can be used in cases in which crosslinking technology is used by melting and then solidifying a saccharide.

The "saccharide of low moldability" means a saccharide that provides a tablet hardness of 0 to 2 kp when, for instance, 150 mg of saccharide are tableted at a tableting pressure of 10 to 50 kg/cm$^2$ using a punch with a diameter of 8 mm. Moreover, a "saccharide with a high moldability" means a saccharide that shows a hardness by the same method of 2 kp or higher. The saccharide of low moldability is pharmaceutically acceptable. Examples are lactose, mannitol, glucose, sucrose, xylitol, erythritol, and the like. One or a combination of two or more of these can be used. The saccharide of high moldability is a pharmaceutically acceptable saccharide. Examples are maltose, maltitol, sorbitol, trehalose, and the like. One or a combination of two or more of these can be used.

The "crystalline saccharide" is a pharmaceutically acceptable saccharide. Examples are mannitol, maltitol, erythritol, xylitol, and the like. One or a combination of two or more of these saccharides can be used. The "amorphous saccharide" is a pharmaceutically acceptable saccharide. Examples are lactose, sucrose, glucose, sorbitol, maltose, trehalose, and the like. One or a combination of two or more of these can be used.

Moreover, the "filler with a melting point that is higher than the saccharide with a low melting point" is a pharmaceutically acceptable filler, and can be selected from xylitol, trehalose, maltose, sorbitol, erythritol, glucose, sucrose, maltitol, mannitol, and the like. One or a combination of two or more of these saccharides can be used as needed. The "saccharide with a low melting point" is a pharmaceutically acceptable saccharide, and can be selected from xylitol, trehalose, maltose, sorbitol, erythritol, glucose, sucrose, inaltitol, mannitol, and the like. One or a combination of two or more of these saccharides can be used. Maltitol, copolyvidone, and the like are examples of the binder for the fast-disintegrating tablets. One or a combination of two or more binders can be used as needed.

Preferred examples of water-soluble polymers that can be used in place of the saccharide of high moldability are hydroxypropylcellulose, hydroxypropylmethylcellulose, povidone, polyvinyl alcohol, powdered acacia, gelatin, pullulan, and the like.

The amount of filler used in the fast-disintegrating tablets containing the pharmaceutical composition in particle form of the present invention is adjusted as needed in accordance with the amount of pharmaceutical composition in particle form of the present invention and/or size of the tablet, and the like, but usually is 20 to 1,000 mg per tablet, preferably 50 to 900 mg per tablet, particularly 100 to 800 mg per tablet.

Moreover, the amount of saccharide of high moldability, water-soluble polymer, amorphous saccharide, and saccharide with a low melting point differs with the individual technology, but is 0.5 to 40 wt %, preferably 2 to 30 wt %, particularly 5 to 20 wt %, in terms of the weight of filler, or ideally, 1 to 20 wt % in terms of the entire pharmaceutical preparation.

The type of other additives, how they are added, and the amount added are given in the above-mentioned patent references on fast-disintegrating tablets that were referred to in the present specification.

Moreover, when the pharmaceutical composition in particle form of the present invention is contained in the fast-disintegrating tablets, the tablets can contain the pharmaceutical composition in particle form to the equivalent of 0.5 to 90 wt % of the entire fast-disintegrating tablet. The equivalent of 1 to 80 wet % is preferred, and the equivalent of 5 to 60 wt % is particularly preferred.

The method for producing the pharmaceutical composition in particle form of the present invention will be described below.

Core particles containing a drug are coated with a middle layer and a layer for controlling water permeation in order to obtain the pharmaceutical composition in particle form of the present invention. Particles composed of a drug only can also be used as the core particles containing a drug. Moreover, it is also possible to make and use particles composed of a drug and one or more additives using prior art. The particles composed of a drug and additives can be made by mixing a drug and an appropriate filler (for instance, microcrystalline cellulose, lactose, corn starch, and the like), adding binder (for instance, hydroxypropylcellulose, and the like) as needed, and granulating, sizing, and drying the mixture. A liquid in which a drug and binder have been dissolved or dispersed can also be sprayed on additive particles that serve as the core (for instance, micro crystalline cellulose spheres, sucrose spheres, sucrose starch spheres, and the like). A liquid in which the drug and appropriate fillers have been dissolved or suspended can also be sprayed and dried.

Any method with which it is possible to coat a pharmaceutical composition in particle form, such as a fluidized bed coating machine, a rotary fluidized coating machine, or a centrifugal coating machine, can be used as the method for coating the core particles containing a drug with a middle layer and a layer for controlling water penetration. For instance, the necessary amount of liquid containing coating components can be sprayed with a spray gun on the core particles containing a drug as they are circulated by warm air in a fluidized bed side-spraying coating machine. The liquid containing the coating components is prepared by dissolving or dispersing the essential components in water, ethanol, methanol, or another solvent. Moreover, these solvents can be used as a mixture as needed.

The method for producing fast-disintegrating tablets containing the pharmaceutical composition in particle form of the present invention will now be described below.

An example is the fast-disintegrating tablets in International Publication 95-20380 (corresponding U.S. Pat. No. 5,576,014 Specification). The steps can be used whereby the pharmaceutical composition in particle form of the present invention and a saccharide of low moldability are mixed, this mixture is coated and/or granulated by spraying a saccharide of high moldability as the binder, and this granulated product is compressed. A humidification and drying step can be used to increase hardness of the molded products that have been prepared. Although determined by the apparent critical relative humidity of the saccharide contained in the product, "humidification" is usually humidification to the critical relative humidity or higher. For instance, humidity is 30 to 100% RH, preferably 50 to 90% RH. Temperature at this time is preferably 15 to 50° C., particularly 20 to 40° C. Treatment time is 1 to 36 hours, preferably 12 to 24 hours. There are no special restrictions to the "drying" as long as it is a step whereby the moisture absorbed by humidification is removed. For instance, the drying temperature can be set at 10 to 100° C., preferably 20 to 60° C., particularly 25 to 40° C. Treatment time can be hours, preferably 1 to 4 hours.

Another example is the fast-disintegrating tablets cited in International Publication 2002-92057 (corresponding U.S. p application Early Disclosure 2003/099701 Specification). The pharmaceutical composition in particle form of the present invention, filler with a high melting point, and saccharide with a low melting point can be mixed, this mixture can be applied by coating and/or granulated by being sprayed with a binder for fast-disintegrating tablets, and the granulated product can be compressed. When a filler with a high melting point and a saccharide with a low melting point are combined, a heating step can also be used in order to increase hardness of the compressed product that has been prepared. Although determined by the melting point of the saccharide with a low melting point contained in the tablets, the "heating" is usually heating to a temperature that is the melting point of the saccharide with a low melting point or higher, but less than the melting point of the filler with a high melting point. Treatment time can be 0.5 to 120 minutes, preferably 1 to 60 minutes.

PREFERRED EMBODIMENTS OF THE INVENTION

Figure 1:
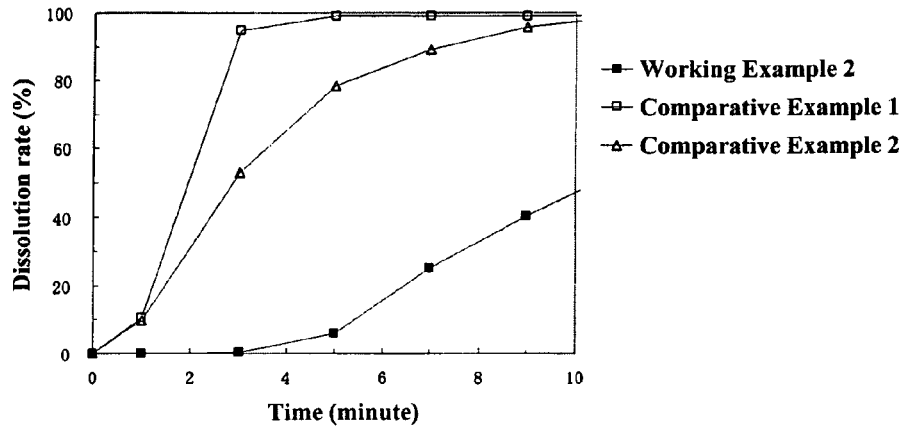
FIG. 1 shows the dissolution profiles obtained by dissolution tests of the pharmaceutical compositions in particle form of Working Example 2 and Comparative Examples 1 and 2.
Figure 2:
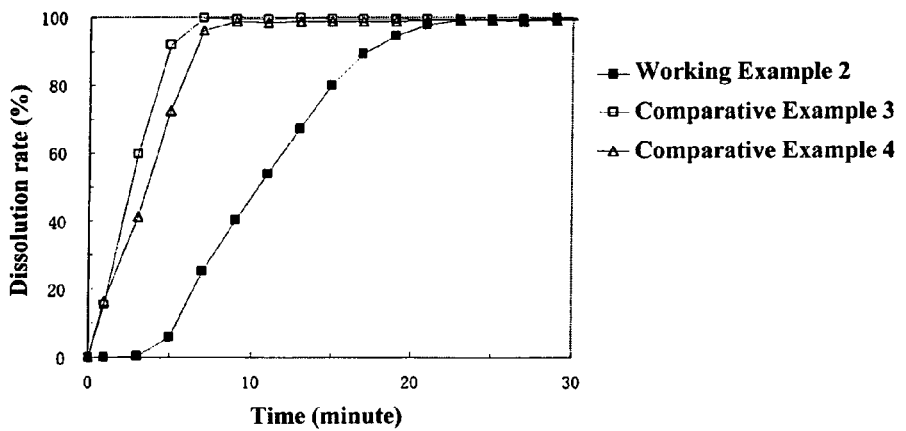
FIG. 2 shows the dissolution profiles obtained by dissolution tests of the pharmaceutical compositions in particle form of Working Example 2 and Comparative Examples 3 and 4.
Figure 3:
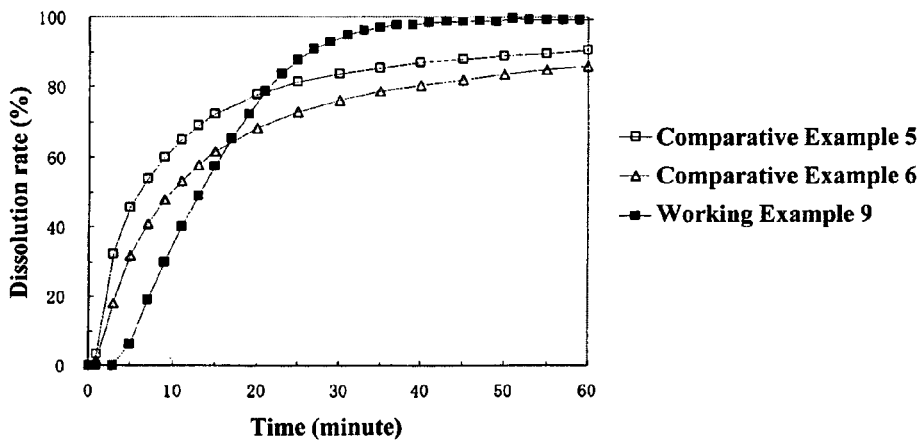
FIG. 3 shows the dissolution profiles obtained by dissolution tests of the pharmaceutical compositions in particle form of Working Example 9 and Comparative Examples 5 and 6.
Figure 4:
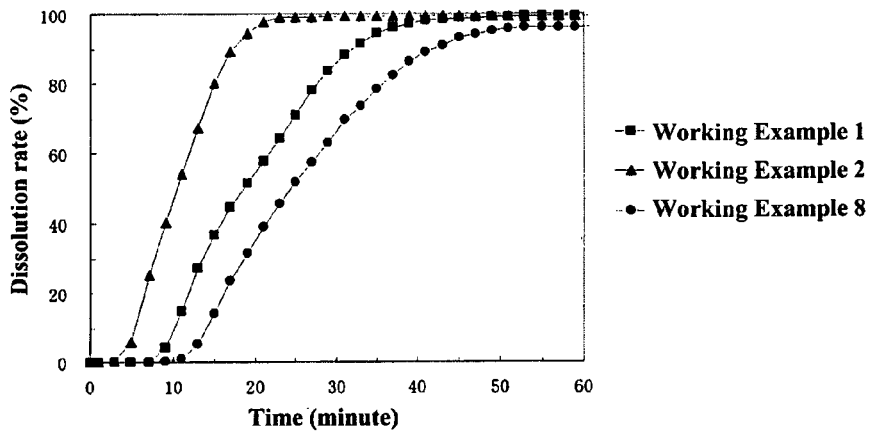
FIG. 4 shows the dissolution profiles obtained by dissolution tests of the pharmaceutical compositions in particle form of Working Examples 1, 2, and 8.
Figure 5:
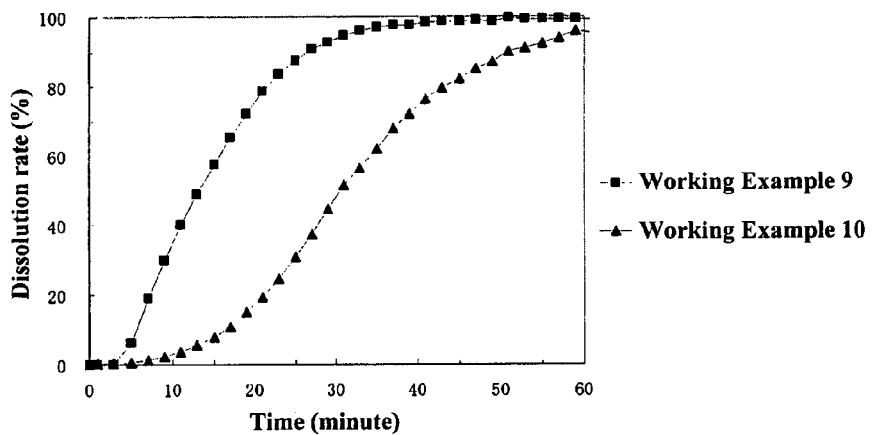
FIG. 5 shows the dissolution profiles obtained by dissolution tests of the pharmaceutical compositions in particle form of Working Examples 9 and 10.
Figure 6:
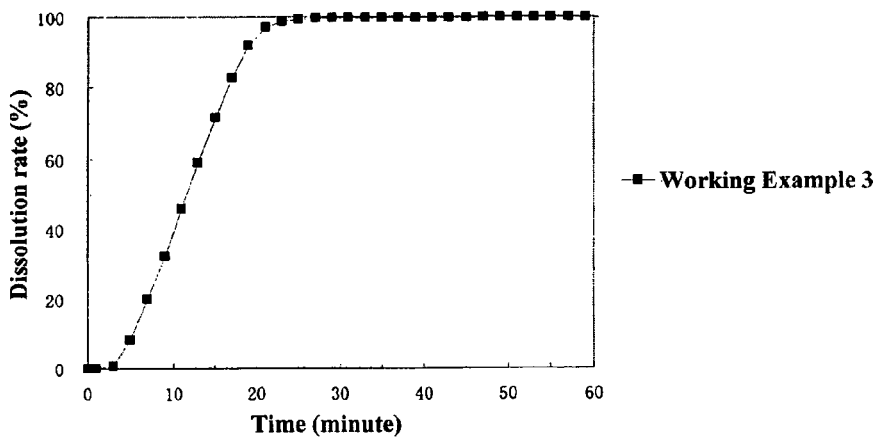
FIG. 6 shows the dissolution profiles obtained by dissolution tests of the pharmaceutical composition in particle form of Working Example 3.
Figure 7:
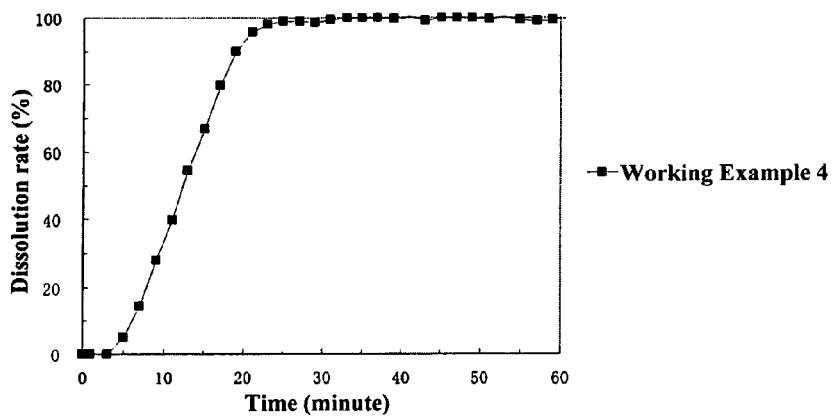
FIG. 7 shows the dissolution profiles obtained by dissolution tests of the pharmaceutical composition in particle form of Working Example 4.
Figure 8:
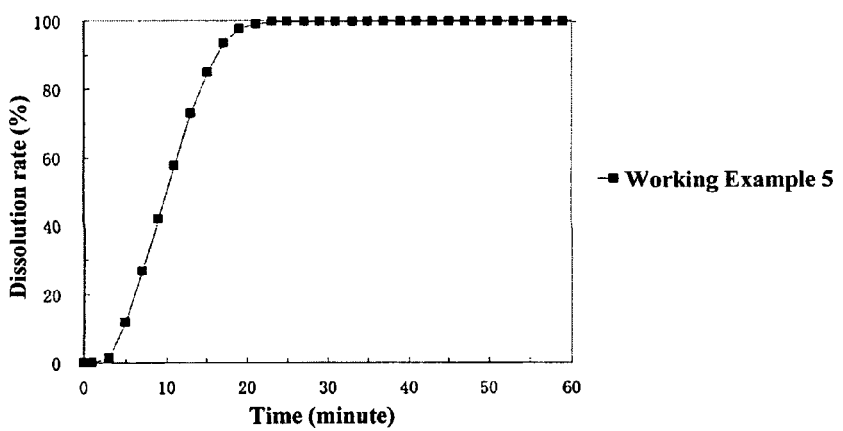
FIG. 8 shows the dissolution profiles obtained by dissolution tests of the pharmaceutical composition in particle form of Working Example 5.
Figure 9:
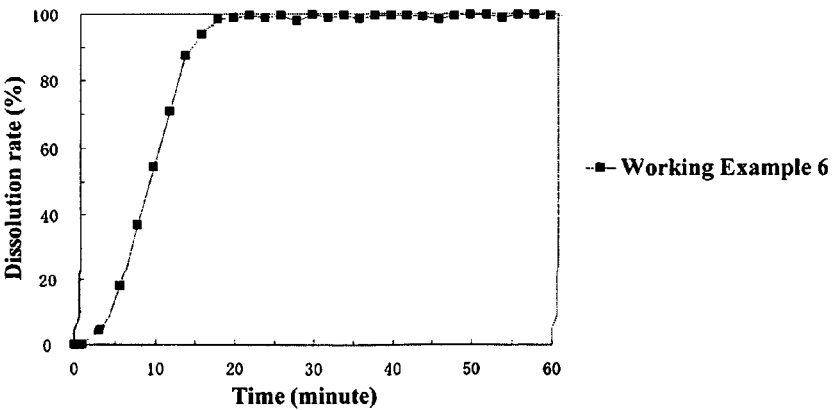
FIG. 9 shows the dissolution profiles obtained by dissolution tests of the pharmaceutical composition in particle form of Working Example 6.
Figure 10:
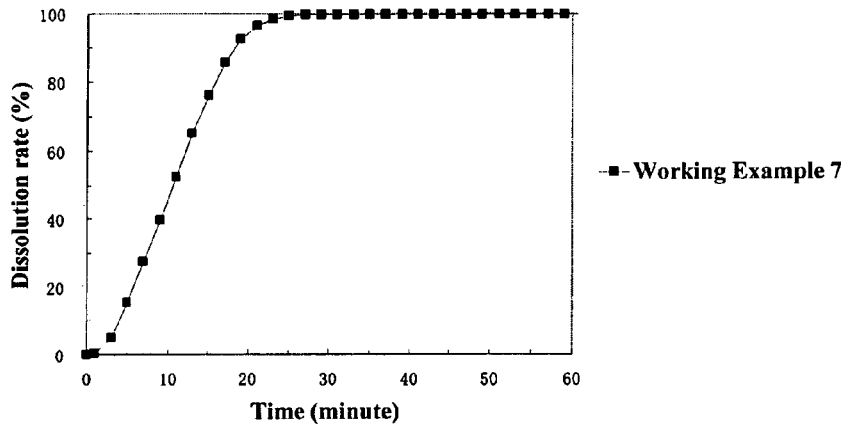
FIG. 10 shows the dissolution profiles obtained by dissolution tests of the pharmaceutical composition in particle form of Working Example 7.
Figure 11:
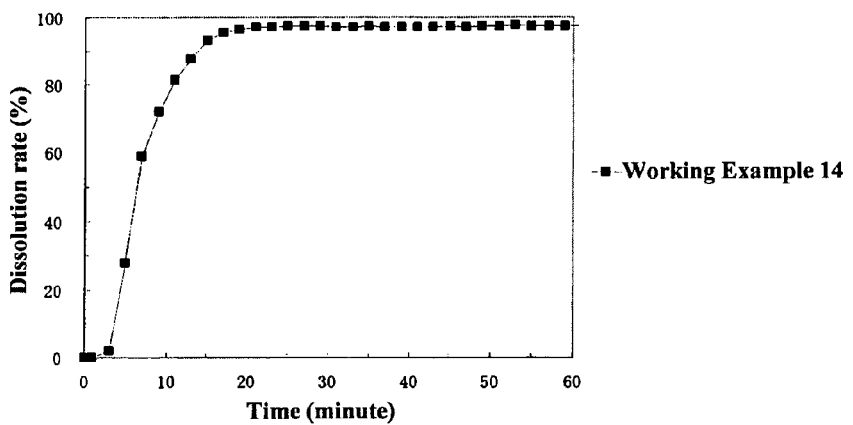
FIG. 11 shows the dissolution profiles obtained by dissolution tests of the pharmaceutical composition in particle form of Working Example 14.
Figure 12:
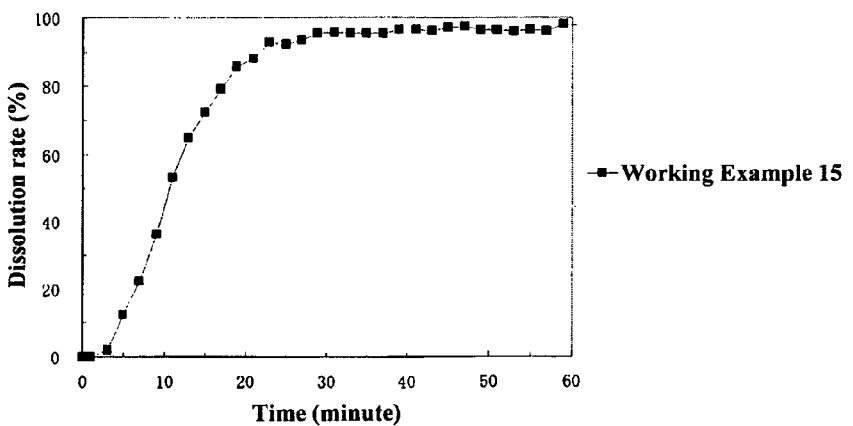
FIG. 12 shows the dissolution profiles obtained by dissolution tests of the pharmaceutical composition in particle form of Working Example 15.
Figure 13:
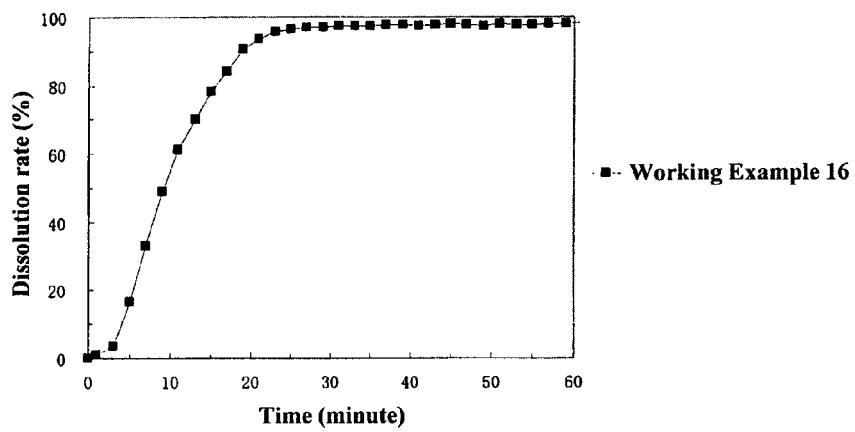
FIG. 13 shows the dissolution profiles obtained by dissolution tests of the pharmaceutical composition in particle form of Working Example 16.

The present invention will be described in specific terms using working examples, but the scope of the present invention is not limited by these working examples.

Working Example 1

Preparation of Core Particles Containing a Drug

A liquid of 225.0 g of acetaminophen (Yoshitomi Fine Chemicals, Ltd.) and 22.5 g of hydroxypropylmethylcellulose 2910 (Shin-Etsu Chemical Co., Ltd., TC-5E, the same hereafter) dissolved in a mixture of 750.0 g of methanol (Kanto Kagaku, the same hereafter) and 653.0 g of methylene chloride (Kanto Kagaku, the same hereafter) was sprayed from the side onto 750.0 g of sucrose spheres (Freund GmbH; Nonpareil 103 (24-32)) at a product temperature of 30° C., liquid feed rate of 20 g/mL, and spraying air pressure of 2.5 kg/cm using a fluidized bed granulator (Glatt GmbH; GPCG-1, the same hereafter) to obtain core particles containing a drug.

Preparation of Middle Layer Coating Liquid 44.2 g of hydroxypropylmethylcellulose 2910 were dissolved in a mixture of 1052.0 g of methanol and 450.8 g of methylene chloride, 221.0 g of sodium carbonate (Kanto Kagaku, the same hereafter) pulverized with a jet mill pulverizer (Hosokawa Micron Corporation; Spiral Jet Mill 50AS, the same hereafter) were added, and the product was stirred to prepare the middle layer coating liquid.

Preparation of Particles Coated with Middle Layer

The above-mentioned middle layer coating liquid was sprayed from the side onto 500.0 g of the above-mentioned core particles containing a drug at a product temperature of 30° C., liquid feed rate of 20 g/min, and a spraying air pressure of 4.5 kg/cm using a fluidized bed granulator to obtain particles coated with a middle layer wherein core particles containing a drug were coated with a 53 wt % middle layer.

The average particle diameter of the resulting particles, coated with a middle layer was 730 µm.

Preparation of Coating Liquid for Layer for Controlling Water Penetration 40.0 g of cetanol (Kao Corporation; Kalcol 6098, the same hereafter) were dissolved in 1560.0 g of methylene chloride to prepare the coating liquid for the layer for controlling water penetration.

Preparation of Particles Coated with Middle Layer and Layer for Controlling Water Penetration The above-mentioned coating liquid for the layer for controlling water penetration was sprayed from the side onto 500.0 g of particles coated with a middle layer at a product temperature of 30° C., liquid feed rate of 15 g/min, and spraying air pressure of 2.0 kg/cm$^2$ using a fluidized bed granulator to obtain particles coated with a middle layer and a layer for controlling water penetration wherein the particles coated with a middle layer were coated with an 8 wt % layer for controlling water penetration. The average particle diameter of the resulting particles coated with a middle layer and a layer for controlling water penetration was 777 µm.

Working Example 2

Preparation of Coating Liquid for Controlling Water Penetration 25.0 g of cetanol were dissolved in 975.0 g of methylene chloride to prepare the coating liquid for the layer for controlling water penetration.

Preparation of Particles Coated with Middle Layer and Layer for Controlling Water Penetration The above-mentioned coating liquid for a layer for controlling water penetration was sprayed from the side onto 500.0 g of particles coated with a middle layer obtained in Working Example 1 at a product temperature of 30° C., liquid feed rate of 15 g/min, and a spraying air pressure of 2.0 kg/cm$^2$ using a fluidized bed granulator to obtain particles coated with a middle layer and a layer for controlling water penetration wherein the particles coated with a middle layer were coated with a 5 wt % layer for controlling water penetration. The average particle diameter of the resulting particles coated with a middle layer and a layer for controlling water penetration was 760 µm.

Working Example 3

Preparation of Middle Layer Coating Liquid 39.8 g of hydroxypropylmethylcellulose 2910 were dissolved in a mixture of 946.8 g of methanol and 405.8 g of methylene chloride, 198.9 g of sodium dihydrogen phosphate dihydrate (Kanto Kagaku, the same hereafter) pulverized with a jet mill pulverizer were added, and the product was stirred to prepare the middle layer coating liquid.

Preparation of Particles Coated with Middle Layer

The above-mentioned middle layer coating liquid was sprayed from the side onto 450.0 g of core particles containing a drug obtained in Working Example 1 at a product temperature of 30° C., liquid feed rate of 22.0 g/min, and a spraying air pressure of 4.5 kg/cm$^2$ using a fluidized bed granulator to obtain particles coated with a middle layer wherein core particles containing a drug were coated with a 53 wt % middle layer. The average particle diameter of the resulting particles coated with a middle layer was 889 µm.

Preparation of Coating Liquid for Layer for Controlling Water Penetration 25.0 g of cetanol were dissolved in 975.0 g of methylene chloride to prepare the coating liquid for the layer for controlling water penetration.

Preparation of Particles Coated with Middle Layer and Layer for Controlling Water Penetration The above-mentioned coating liquid for the layer for controlling water penetration was sprayed from the side onto 500.0 g of particles coated with a middle layer at a product temperature of 30° C., liquid feed rate of 12.5 g/min, and spraying air pressure of 2.5 kg/cm$^2$ using a fluidized bed granulator to obtain particles coated with a middle layer and a layer for controlling water penetration wherein the particles coated with a middle layer were coated with an 5 wt % layer for controlling water penetration. The average particle diameter of the resulting particles coated with a middle layer and a layer for controlling water penetration was 996 µm.

Working Example 4

Preparation of Middle Layer Coating Liquid 39.8 g of hydroxypropylmethylcellulose 2910 were dissolved in a mixture of 946.8 g of methanol and 405.8 g of methylene chloride, 198.9 g of trisodium citrate dihydrate (Kanto Kagaku) pulverized with a jet mill pulverizer were added, and the product was stirred to prepare the middle layer coating liquid.

Preparation of Particles Coated with Middle Layer

The above-mentioned middle layer coating liquid was sprayed from the side onto 450.0 g of core particles containing a drug obtained in Working Example 1 at a product temperature of 30° C., liquid feed rate of 20 g/min, and a spraying air pressure of 5.0 kg/cm$^2$ using a fluidized bed granulator to obtain particles coated with a middle layer wherein core particles containing a drug were coated with a 53 wt % middle layer. The average particle diameter of the resulting particles coated with a middle layer was 948 µm.

Preparation of Coating Liquid for Layer for Controlling Water Penetration 25.0 g of cetanol were dissolved in 975.0 g of methylene chloride to prepare the coating liquid for the layer for controlling water penetration.

Preparation of Particles Coated with Middle Layer and Layer for Controlling Water Penetration The above-mentioned coating liquid for the layer for controlling water penetration was sprayed from the side onto 500.0 g of particles coated with a middle layer at a product temperature of 30° C., liquid feed rate of 21.0 g/min, and spraying air pressure of 2.5 kg/cm$^2$ using a fluidized bed granulator to obtain particles coated with a middle layer and a layer for controlling water penetration wherein the particles coated with a middle layer were coated with a 5 wt % layer for controlling water penetration. The average particle diameter of the resulting particles coated with a middle layer and a layer for controlling water penetration was 1024 μm.

Working Example 5

Preparation of Middle Layer Coating Liquid 44.2 g of hydroxypropylmethylcellulose 2910 were dissolved in a mixture of 1052.0 g of methanol and 450.8 g of methylene chloride, 221.0 g of sodium chloride (Kanto Kagaku) pulverized with a jet mill pulverizer were added, and the product was stirred to prepare the middle layer coating liquid.

Preparation of Particles Coated with Middle Layer

The above-mentioned middle layer coating liquid was sprayed from the side onto 500.0 g of core particles containing a drug obtained in Working Example 1 at a product temperature of 30° C., liquid feed rate of 18.6 g/min, and a spraying air pressure of 4.5 kg/cm$^2$ using a fluidized bed granulator to obtain particles coated with a middle layer wherein core particles containing a drug were coated with a 53 wt % middle layer. The average particle diameter of the resulting particles coated with a middle layer was 913 μm.

Preparation of Coating Liquid for Layer for Controlling Water Penetration 25.0 g of cetanol were dissolved in 975.0 g of methylene chloride to prepare the coating liquid for the layer for controlling water penetration.

Preparation of Particles Coated with Middle Layer and Layer for Controlling Water Penetration The above-mentioned coating liquid for the layer for controlling water penetration was sprayed from the side onto 500.0 g of particles coated with a middle layer at a product temperature of 30° C., liquid feed rate of 16.0 g/min, and spraying air pressure of 2.0 kg/cm$^2$ using a fluidized bed granulator to obtain particles coated with a middle layer and a layer for controlling water penetration wherein the particles coated with a middle layer were coated with a 5 wt % layer for controlling water penetration. The average particle diameter of the resulting particles coated with a middle layer and a layer for controlling water penetration was 1018 μm.

Working Example 6

Preparation of Middle Layer Coating Liquid 39.8 g of hydroxypropylmethylcellulose 2910 were dissolved in a mixture of 946.8 g of methanol and 405.8 g of methylene chloride, 198.9 g of glycine (Kanto Kagaku) pulverized with a jet mill pulverizer were added, and the product was stirred to prepare the middle layer coating liquid.

Preparation of Particles Coated with Middle Layer

The above-mentioned middle layer coating liquid was sprayed from the side onto 450.0 g of core particles containing a drug obtained in Working Example 1 at a product temperature of 30° C., liquid feed rate of 20 g/min, and a spraying air pressure of 5.0 kg/cm$^2$ using a fluidized bed granulator to obtain particles coated with a middle layer wherein core particles containing a drug were coated with a 53 wt % middle layer. The average particle diameter of the resulting particles coated with a middle layer was 1007 μm.

Preparation of Coating Liquid for Layer for Controlling Water Penetration 25.0 g of cetanol were dissolved in 975.0 g of methylene chloride to prepare the coating liquid for the layer for controlling water penetration.

Preparation of Particles Coated with Middle Layer and Layer for Controlling Water Penetration The above-mentioned coating liquid for the layer for controlling water penetration was sprayed from the side onto 500.0 g of particles coated with a middle layer at a product temperature of 30° C., liquid feed rate of 20.0 g/min, and spraying air pressure of 2.5 kg/cm$^2$ using a fluidized bed granulator to obtain particles coated with a middle layer and a layer for controlling water penetration wherein the particles coated with a middle layer were coated with a 5 wt % layer for controlling water penetration. The average particle diameter of the resulting particles coated with a middle layer and a layer for controlling water penetration was 1026 μm.

Working Example 7

Preparation of Middle Layer Coating Liquid 42.0 g of hydroxypropylmethylcellulose 2910 were dissolved in a mixture of 989.0 g of methanol and 424.0 g of methylene chloride, 208.0 g of sucrose (Nisshin Sugar Manufacturing Co., Ltd.; Frost Sugar FS2) pulverized with a jet mill pulverizer were added, and the product was stirred to prepare the middle layer coating liquid.

Preparation of Particles Coated with Middle Layer

The above-mentioned middle layer coating liquid was sprayed from the side onto 470.0 g of core particles containing a drug obtained in Working Example 1 at a product temperature of 30° C., liquid feed rate of 17 g/min, and a spraying air pressure of 4.5 kg/cm$^2$ using a fluidized bed granulator to obtain particles coated with a middle layer wherein core particles containing a drug were coated with a 53 wt % middle layer. The average particle diameter of the resulting particles coated with a middle layer was 1011 μm.

Preparation of Coating Liquid for Layer for Controlling Water Penetration 25.0 g of cetanol were dissolved in 975.0 g of methylene chloride to prepare the coating liquid for the layer for controlling water penetration.

Preparation of Particles Coated with Middle Layer and Layer for Controlling Water Penetration The above-mentioned coating liquid for the layer for controlling water penetration was sprayed from the side onto 500.0 g of particles coated with a middle layer at a product temperature of 30° C., liquid feed rate of 19.0 g/min, and spraying air pressure of 2.0 kg/cm$^2$ using a fluidized bed granulator to obtain particles coated with a middle layer and a layer for controlling water penetration wherein the particles coated with a middle layer were coated with a 5 wt % layer for controlling water penetration. The average particle diameter of the resulting particles coated with a middle layer and a layer for controlling water penetration was 1037 µm.

Working Example 8

Preparation of Middle Layer Coating Liquid 60.0 g of hydroxypropylmethylcellulose 2910 were dissolved in a mixture of 1428.0 g of methanol and 612.0 g of methylene chloride, 300.0 g of sodium carbonate pulverized with a jet mill pulverizer were added, and the product was stirred to prepare the middle layer coating liquid.

Preparation of Particles Coated with Middle Layer

The above-mentioned middle layer coating liquid was sprayed from the side onto 500.0 g of core particles containing a drug obtained in Working Example 1 at a product temperature of 33° C., liquid feed rate of 15 g/min, and a spraying air pressure of 3.5 kg/cm$^2$ using a fluidized bed granulator to obtain particles coated with a middle layer wherein core particles containing a drug were coated with a 72 wt % middle layer. The average particle diameter of the resulting particles coated with a middle layer was 767 µm.

Preparation of Coating Liquid for Layer for Controlling Water Penetration 25.0 g of cetanol were dissolved in 975.0 g of methylene chloride to prepare the coating liquid for the layer for controlling water penetration.

Preparation of Particles Coated with Middle Layer and Layer for Controlling Water Penetration The above-mentioned coating liquid for the layer for controlling water penetration was sprayed from the side onto 500.0 g of particles coated with a middle layer at a product temperature of 31° C., liquid feed rate of 15 g/min, and spraying air pressure of 2.0 kg/cm$^2$ using a fluidized bed granulator to obtain particles coated with a middle layer and a layer for controlling water penetration wherein the particles coated with a middle layer were coated with a 5 wt % layer for controlling water penetration. The average particle diameter of the resulting particles coated with a middle layer and a layer for controlling water penetration was 768 µm.

Comparative Example 1

Preparation of Insolubilizing Substance Layer Coating Liquid 265.0 g of hydroxypropylmethylcellulose 2910 were dissolved in a mixture of 1051.0 g of methanol and 451.0 g of methylene chloride to prepare the insolubilizing substance layer coating liquid.

Preparation of Particles Coated with Insolubilizing Substance Layer

The above-mentioned insolubilizing substance layer coating liquid was sprayed from the side onto 500.0 g of core particles containing a drug obtained in Working Example 1 at a product temperature of 30° C., liquid feed rate of 16 g/min, and a spraying air pressure of 4.5 kg/cm$^2$ using a fluidized bed granulator to obtain particles coated with an insolubilizing substance layer wherein core particles containing a drug were coated with a 53 wt % insolubilizing substance layer. The average particle diameter of the resulting particles coated with an insolubilizing substance layer was 781 µm.

Comparative Example 2

Preparation of Middle Layer Coating Liquid 44.2 g of hydroxypropylmethylcellulose 2910 were dissolved in a mixture of 1052.0 g of methanol and 450.8 g of methylene chloride, 221.0 g of sodium carbonate pulverized with a jet mill pulverizer were added, and the product was stirred to prepare the middle layer coating liquid.

Preparation of Particles Coated with Middle Layer

The above-mentioned middle layer coating liquid was sprayed from the side onto 500.0 g of core particles containing a drug obtained in Working Example 1 at a product temperature of 30° C., liquid feed rate of 19.2 g/min, and a spraying air pressure of 4.5 kg/cm$^2$ using a fluidized bed granulator to obtain particles coated with a middle layer wherein core particles containing a drug were coated with a 53 wt % middle layer. The average particle diameter of the resulting particles coated with a middle layer was 730 µm.

Comparative Example 3

Preparation of Insolubilizer Layer Coating Liquid 238.7 g of sodium carbonate were dissolved in 1352.5 g of purified water to prepare the insolubilizer layer coating liquid.

Preparation of Particles Coated with Insolubilizer Layer

The above-mentioned insolubilizer layer coating liquid was sprayed from the side onto 450.0 g of core particles containing a drug obtained in Working Example 1 at a product temperature of 30° C., liquid feed rate of 17 g/min, and a spraying air pressure of 4.0 kg/cm$^2$ using a fluidized bed granulator to obtain particles coated with a insolubilizer layer wherein core particles containing a drug were coated with a 53 wt % insolubilizer layer. The average particle diameter of the resulting particles coated with a insolubilizer layer was 917 µm.

Preparation of Coating Liquid for Layer for Controlling Water Penetration 36.0 g of cetanol were dissolved in 1404.0 g of methylene chloride to prepare the coating liquid for the layer for controlling water penetration.

Preparation of Particles Coated with Insolubilizer Layer and Layer for Controlling Water Penetration The above-mentioned coating liquid for the layer for controlling water penetration was sprayed from the side onto 450.0 g of particles coated with an insolubilizer layer at a product temperature of 30° C., liquid feed rate of 20 g/min, and spraying air pressure of 2.5 kg/cm$^2$ using a fluidized bed granulator to obtain particles coated with an insolubilizer layer and a layer for controlling water penetration wherein the particles coated with an insolubilizer layer were coated with an 8 wt % layer for controlling water penetration. The average particle diameter of the resulting particles coated with a insolubilizer layer and a layer for controlling water penetration was 1085 µm.

Comparative Example 4

Preparation of Coating Liquid for Layer for Controlling Water Penetration 40.0 g of cetanol were dissolved in 1560.0 g of methylene chloride to prepare the coating liquid for the layer for controlling water penetration.

Preparation of Particles Coated with Insolubilizing Substance Layer and Layer for Controlling Water Penetration The above-mentioned coating liquid for the layer for controlling water penetration was sprayed from the side onto 500.0 g of particles coated with an insolubilizing substance layer obtained in Comparative Example 1 at a product temperature of 30° C., liquid feed rate of 12 g/min, and spraying air pressure of 2.0 kg/cm using a fluidized bed granulator to obtain particles coated with an insolubilizing substance layer and a layer for controlling water penetration wherein the particles coated with an insolubilizing substance layer were coated with an 8 wt % layer for controlling water penetration. The average particle diameter of the resulting particles coated with a insolubilizing substance layer and a layer for controlling water penetration was 786 µm.

Comparative Example 5

Preparation of Core Particles Containing a Drug

A liquid of 600.0 g of imipramine hydrochloride (Man Mill Chemicals, the same hereafter) and 60.0 g of hydroxypropylmethylcellulose 2910 dissolved in 2640.0 g of purified water was sprayed from the side onto 300.0 g of microcrystalline cellulose spheres (Asahi Kasei Chemicals Corporation; CP-102Y, the same hereafter) at a product temperature of 25° C., liquid feed rate of 7.8 g/min, and spraying air pressure of 3.0 kg/cm$^2$ using a fluidized bed granulator to obtain core particles containing a drug.

Preparation of Coating Liquid for Layer for Controlling Water Penetration 4.2 g of hydroxypropylmethylcellulose 2910 were uniformly dissolved in 12.0 g of purified water, 387.0 g of methanol were added, and 16.8 g of ethylcellulose (Dow Chemical Company; Ethocel, standard 10 premium, the same hereafter) were dissolved in the mixture.

Preparation of Particles Coated with Layer for Controlling Water Penetration

The above-mentioned coating liquid for the layer for controlling water penetration was sprayed from the side onto 300.0 g of the above-mentioned core particles containing a drug at a product temperature of 40° C., liquid feed rate of 5.5 g/min, and a spraying air pressure of 2.0 kg/cm$^2$ using a fluidized bed granulator to obtain particles coated with a layer for controlling water penetration wherein core particles containing a drug were coated with a 7 wt % layer for controlling water penetration. The average particle diameter of the resulting particles coated with a layer for controlling water penetration was 210 µm.

Comparative Example 6

Preparation of Coating Liquid for Layer for Controlling Water Penetration 6.0 g of hydroxypropylmethylcellulose 2910 were uniformly dissolved in 17.1 g of purified water, 553.9 g of methanol were added, and 24.0 g of ethylcellulose were dissolved in the mixture.

Preparation of Particles Coated with Layer for Controlling Water Penetration

The above-mentioned coating liquid for the layer for controlling water penetration was sprayed from the side onto 300.0 g of the core particles containing a drug obtained in Comparative Example 5 at a product temperature of 40° C., liquid feed rate of 5.5 g/min, and a spraying air pressure of 2.0 kg/cm$^2$ using a fluidized bed granulator to obtain particles coated with a layer for controlling water penetration wherein core particles containing a drug were coated with a 10 wt % layer for controlling water penetration. The average particle diameter of the resulting particles coated with a layer for controlling water penetration was 211 µm.

Working Example 9

Preparation of Middle Layer Coating Liquid 100.0 g of hydroxypropylmethylcellulose 2910 were dissolved in a mixture of 2380.0 g of methanol and 1020.0 g of methylene chloride, 500.0 g of sodium carbonate pulverized with a jet mill pulverizer were added, and the product was stirred to prepare the middle layer coating liquid.

Preparation of Particles Coated with Middle Layer

The above-mentioned middle layer coating liquid was sprayed from the side onto 400.0 g of core particles containing a drug obtained in Comparative Example 5 at a product temperature of 50° C., liquid feed rate of 13 g/min, and a spraying air pressure of 5.0 kg/cm$^2$ using a fluidized bed granulator to obtain particles coated with a middle layer wherein core particles containing a drug were coated with a 150 wt % middle layer. The average particle diameter of the resulting particles coated with a middle layer was 253 µm.

Preparation of Coating Liquid for Layer for Controlling Water Penetration 1.0 g of triethyl citrate (Pfizer Inc.; Citroflex 2 SC-60, the same hereafter) and 10.0 g of aminoalkyl methacrylate copolymer RS (Rohm GmbH; Eudragit RS100, the same hereafter) were dissolved in 304.0 g of methylene chloride, and 5.0 g of talc (Kihara Kasei Co., Ltd., the same hereafter) were added to this mixture to prepare the coating liquid for the layer for controlling water penetration.

Preparation of Particles Coated with Middle Layer and Layer for Controlling Water Penetration The above-mentioned coating liquid for the layer for controlling water penetration was sprayed from the side onto 400.0 g of particles coated with a middle layer at a product temperature of 40° C., liquid feed rate of 10 g/min, and spraying air pressure of 4.0 kg/cm² using a fluidized bed granulator to obtain particles coated with a middle layer and a layer for controlling water penetration wherein the particles coated with a middle layer were coated with a 4 wt % layer for controlling water penetration. The average particle diameter of the resulting particles coated with a middle layer and a layer for controlling water penetration was 259 µm.

Working Example 10

Preparation of Coating Liquid for Layer for Controlling Water Penetration 1.8 g of triethyl citrate and 17.5 g of aminoalkyl methacrylate copolymer RS were dissolved in 532.0 g of methylene chloride, and 8.8 g of talc were added to this mixture to prepare the coating liquid for the layer for controlling water penetration.

Preparation of Particles Coated with Middle Layer and Layer for Controlling Water Penetration The above-mentioned coating liquid for the layer for controlling water penetration was sprayed from the side onto 400.0 g of the particles coated with a middle layer obtained in Working Example 9 at a product temperature of 40° C., liquid feed rate of 10 g/min, and spraying air pressure of 4.0 kg/cm² using a fluidized bed granulator to obtain particles coated with a middle layer and a layer for controlling water penetration wherein the particles coated with a middle layer were coated with a 7 wt % layer for controlling water penetration. The average particle diameter of the resulting particles coated with a middle layer and a layer for controlling water penetration was 264 µm.

Working Example 11

Preparation of Fast-disintegrating Tablets Containing Particles Coated with a Middle Layer and Layer for Controlling Water Penetration A mixture of 247.6 g of mannitol (Towa Kasei Co., Ltd.; Mannit P, the same hereafter) pulverized with a pin mill (Hosokawa Micron Corporation; Fine Impact Mill 100UPZ, the same hereafter) and sifted with a 42 mesh sieve and 60.0 g of particles coated with a middle layer and a layer for controlling water penetration obtained in Working Example 9 were granulated with 208.3 g of an aqueous solution containing 62.5 g of maltose (Hayashibara Co., Ltd.; Sunmalt S, the same hereafter) using a fluidized bed granulator to obtain granulated particles for fast-disintegrating tablets. 14.4 mg of peppermint flavor (T. Hasegawa Co., Ltd.), 14.4 mg of aspartame (Ajinomoto Co., Inc.), and 3.0 mg of magnesium stearate (Merck & Co., Inc., the same hereafter) were added to 568.2 mg of the above-mentioned granulated particles, the mixture was filled into a die with a diameter of 13 mm, and tableting was performed at a pressure of 1.25 kN using an autograph (Shimadzu Corporation; AGS-20KNG, the same hereafter) to make tablets. These tablets were stored for 18 hours at 25° C. (relative humidity of 75%) using a thermostatic constant-humidity chamber (Tabaiespec Co., Ltd.; PR-35C, the same hereafter) and then stored for three hours at 30° C. (relative humidity of 40%) to make fast-disintegrating tablets. These fast-disintegrating tablets disintegrated in the oral cavity in 25 seconds.

Working Example 12

Preparation of Core Particles Containing a Drug

A liquid of 476.2 g of imipramine hydrochloride and 47.6 g of hydroxypropylmethylcellulose 2910 dissolved in a mixture of 1257.0 g of methanol and 838.0 g of purified water was sprayed from the side onto 476.2 g of microcrystalline cellulose spheres at a product temperature of 35° C., liquid feed rate of 12.4 g/min, and spraying air pressure of 3.5 kg/cm² using a fluidized bed granulator to obtain core particles containing a drug.

Preparation of Particles Coated with Middle Layer

A liquid of 27.5 g of hydroxypropylmethylcellulose 2910 dissolved in a mixture of 261.3 g of methanol and 261.3 g of purified water was sprayed from the side onto 275.0 g of the above-mentioned core particles containing a drug at a product temperature of 43° C., liquid feed rate of 10.8 g/min, and spraying air pressure of 3.5 kg/cm² using a fluidized bed granulator. A coating liquid of 112.5 g of sodium carbonate and 22.5 g of povidone (BASF GmbH; Povidone K30, the same hereafter) dissolved in 2022.1 g of purified water was sprayed from the side onto 270.5 g of the resulting particles at a product temperature of 40° C., liquid feed rate of 13.6 g/min, and a spraying air pressure of 3.0 kg/cm² using a fluidized bed granulator to obtain particles coated with a middle layer.

Preparation of Particles Coated with Middle Layer and Layer for Controlling Water Penetration A liquid of 27.0 g of povidone dissolved in a mixture of 256.5 g of methanol and 256.5 g of purified water was sprayed from the side onto 270.0 g of the above-mentioned particles coated with a middle layer at a product temperature of 45° C., liquid feed rate of 8.6 g/min, and a spraying air pressure of 3.0 kg/cm² using a fluidized bed granulator. A coating liquid obtained by dissolving 1.4 g of triethyl citrate and 17.1 g of aminoalkyl methacrylate copolymer RS in 515.1 g of methylene chloride and then adding 8.6 g of talc was sprayed from the side onto 271.1 g of the resulting particles at a product temperature of 35° C., liquid feed rate of 8.2 g/min, and spraying air pressure of 3.0 kg/cm² using a fluidized bed granulator to obtain particles coated with a middle layer and a layer for controlling water penetration. The average particle diameter of the resulting particles coated with a middle layer and a layer for controlling water penetration was 213 µm.

Working Example 13

Preparation of Core Particles Containing a Drug

A liquid of 476.2 g of imipramine hydrochloride and 47.6 g of hydroxypropylmethylcellulose 2910 dissolved in a mixture of 1257.0 g of methanol and 838.0 g of purified water was sprayed from the side onto 476.2 g of microcrystalline cellulose spheres at a product temperature of 35° C., liquid feed rate of 12.4 g/min, and spraying air pressure of 3.5 kg/cm² using a fluidized bed granulator to obtain core particles containing a drug. A liquid of 35.0 g of povidone dissolved in a mixture of 332.5 g of methanol and 332.5 g of purified water was sprayed from the side onto 350.0 g of the resulting particles at a product temperature of 42° C., liquid feed rate of 5.2 g/min, and spraying air pressure of 2.0 kg/cm² using a fluidized bed granulator.

Preparation of Particles Coated with Middle Layer

A coating liquid of 141.6 g of sodium carbonate and 28.4 g of povidone dissolved in 2258.6 g of purified water was sprayed from the side onto 340.0 g of the resulting particles at a product temperature of 40° C., liquid feed rate of 10.0 g/min, and spraying air pressure of 3.3 kg/cm$^2$ using a fluidized bed granulator. A coating liquid of 36.0 g of hydroxypropylmethylcellulose 2910 dissolved in a mixture of 342.0 g of methanol and 342.0 g of purified water was sprayed from the side onto 360.0 g of the resulting particles at a product temperature of 41° C., liquid feed rate of 10.4 g/min, and a spraying air pressure of 3.5 kg/cm$^2$ using a fluidized bed granulator to obtain particles coated with a middle layer.

Preparation of Particles Coated with Middle Layer and Layer for Controlling Water Penetration A coating liquid obtained by dissolving 1.6 g of triethyl citrate and 18.9 g of aminoalkyl methacrylate copolymer RS in 570.0 g of methylene chloride and adding 9.0 g of talc was sprayed from the side onto 300.0 g of the particles coated with a middle layer at a product temperature of 35° C., liquid feed rate of 7.6 g/min, and a spraying air pressure of 2.0 kg/cm$^2$ using a fluidized bed granulator to obtain particles coated with a middle layer and a layer for controlling water penetration. The average particle diameter of the resulting particles coated with a middle layer and a layer for controlling water penetration was 215 μm.

Working Example 14

Preparation of Core Particles Containing a Drug

A liquid of 333.3 g of solifenacin succinate (Astellas Pharma Inc.) and 111.1 g of macrogol 6000 (Sanyo Kasei Co., Ltd., the same hereafter) dissolved in a mixture of 552.6 g of methanol and 552.6 g of purified water was sprayed from the side onto 555.6 g of microcrystalline cellulose spheres at a product temperature of 45° C., liquid feed rate of 6.8 g/min, and spraying air pressure of 3.0 kg/cm$^2$ using a fluidized bed granulator to obtain core particles containing a drug.

Preparation of Particles Coated with Middle Layer

A coating liquid of 94.3 g of monobasic sodium phosphate dihydrate and 72.5 g of polyvinyl alcohol-polyethylene glycol graft copolymer (BASF Aktiengesellschaft; Kollicoat IR) dissolved in 1283.3 g of purified water was sprayed from the side onto 290.0 g of the above-mentioned core particles containing a drug at a product temperature of 43° C., liquid feed rate of 7.2 g/min, and spraying air pressure of 0.23 MPa using a fluidized bed granulator to obtain particles coated with a middle layer.

Preparation of Particles Coated with Middle Layer and Layer for Controlling Water Penetration A coating liquid obtained by dissolving 0.9 g of triethyl citrate and 8.8 g of aminoalkyl methacrylate copolymer RS in 266.0 g of methanol and adding 4.4 g of talc was sprayed from the side onto 200.0 g of the particles coated with a middle layer at a product temperature of 26° C., liquid feed rate of 4.9 g/min, and a spraying air pressure of 0.21 MPa using a fluidized bed granulator to obtain particles coated with a middle layer and a layer for controlling water penetration. The average particle diameter of the resulting particles coated with a middle layer and a layer for controlling water penetration was 218 μm.

Working Example 15

Preparation of Particles Coated with Middle Layer

A coating liquid of 94.3 g of monobasic sodium phosphate dihydrate and 72.5 g of hydroxypropylcellulose (Nippon Soda Co., Ltd.; HPC-SL, the same hereafter) dissolved in 1283.3 g of purified water was sprayed from the side onto 290.0 g of the core particles containing a drug obtained in Working Example 14 at a product temperature of 43° C., liquid feed rate of 7.4 g/min, and spraying air pressure of 0.23 MPa using a fluidized bed granulator to obtain particles coated with a middle layer.

Preparation of Particles Coated with Middle Layer and Layer for Controlling Water Penetration A coating liquid obtained by dissolving 1.1 g of triethyl citrate and 11.3 g of aminoalkyl methacrylate copolymer RS in 342.0 g of methanol and adding 5.6 g of talc was sprayed from the side onto 200.0 g of the particles coated with a middle layer at a product temperature of 25° C., liquid feed rate of 5.0 g/min, and a spraying air pressure of 0.21 MPa using a fluidized bed granulator to obtain particles coated with a middle layer and a layer for controlling water penetration. The average particle diameter of the resulting particles coated with a middle layer and a layer for controlling water penetration was 221 μm.

Working Example 16

Preparation of Particles Coated with Middle Layer

A coating liquid of 94.3 g of monobasic sodium phosphate dihydrate and 72.5 g of partially hydrolyzed polyvinyl alcohol (Nippon Synthetic Chemical Industry Co., Ltd.; Gosenol EG-05) dissolved in 1305.0 g of purified water was sprayed from the side onto 290.0 g of the core particles containing a drug obtained in Working Example 14 at a product temperature of 46° C., liquid feed rate of 6.0 g/min, and spraying air pressure of 0.28 MPa using a fluidized bed granulator to obtain particles coated with a middle layer.

Preparation of Particles Coated with Middle Layer and Layer for Controlling Water Penetration A coating liquid obtained by dissolving 1.1 g of triethyl citrate and 11.3 g of aminoalkyl methacrylate copolymer RS in 342.0 g of methanol and adding 5.6 g of talc was sprayed from the side onto 200.0 g of the particles coated with a middle layer at a product temperature of 25° C., liquid feed rate of 5.0 g/min, and a spraying air pressure of 0.21 MPa using a fluidized bed granulator to obtain particles coated with a middle layer and a layer for controlling water penetration. The average particle diameter of the resulting particles coated with a middle layer and a layer for controlling water penetration was 223 μm.

Working Example 17

Preparation of Particles Coated with Middle Layer

A coating liquid of 216.6 g of monobasic sodium phosphate dihydrate and 166.7 g of methylcellulose (Shin-Etsu Chemical Co., Ltd.; Metolose SM-4) dissolved in 4376.8 g of purified water was sprayed from the side onto 666.6 g of the core particles containing a drug obtained in Working Example 14 at a product temperature of 43° C., liquid feed rate of 7.2 g/min, and spraying air pressure of 2.2 kg/cm$^2$ using a fluidized bed granulator to obtain particles coated with a middle layer.

Preparation of Particles Coated with Middle Layer and Layer for Controlling Water Penetration A coating liquid obtained by dissolving 1.1 g of triethyl citrate in 315.8 g of purified water and adding 37.5 g of polyvinyl acetate dispersion stabilized with povidone and sodium lauryl sulfate (BASF Aktiengesellschaft; Kollicoat SR30D) and 5.6 g of talc was sprayed from the side onto 200.0 g of the particles coated with a middle layer at a product temperature of 41° C., liquid feed rate of 5.0 g/min, and a spraying air pressure of 0.20 MPa using a fluidized bed granulator to obtain particles coated with a middle layer and a layer for controlling water penetration. The average particle diameter of the resulting particles coated with a middle layer and a layer for controlling water penetration was 220 μm.

Preparation of Fast-disintegrating Tablets Containing Particles Coated with Middle Layer and Layer for Controlling Water Penetration A mixture of 450.0 g of mannitol pulverized with a pin mill and sifted with a 42 mesh sieve and 90.0 g of the above-mentioned particles coated with a middle layer and a layer for controlling water penetration were granulated with 200.0 g of an aqueous solution containing 60.0 g of maltose to obtain granulated particles for fast-disintegrating tablets.

1.7 mg of magnesium stearate were mixed with 341.7 mg of the above-mentioned granulated particles, the mixture was filled into a die with a diameter of 9.5 mm, and the mixture was tableted at a pressure of 2.0 kN using an autograph to make tablets. These tablets were stored for 18 hours at 25° C. (relative humidity of 65%) and then for 3 hours at 30° C. (relative humidity of 40%) using a thermostatic constant-humidity chamber to make fast-disintegrating tablets. These fast-disintegrating tablets disintegrated in the oral cavity in 17 seconds.

Working Example 18

Preparation of Particles Coated with Middle Layer and Layer for Controlling Water Penetration A coating liquid that was a mixture of a solution comprising 127.0 g of ammonio methacrylate copolymer dispersion, type B (Rohm GmbH; Eudragit RS30D) and 0.4 g of polysorbate 80 (Kanto Kagaku; Tween 80) and a solution comprising 912.3 g of purified water and 31.7 g of ethyl acrylate-methyl methacrylate copolymer dispersion (Rohm GmbH; Eudragit NE30D, the same hereafter) brought to a pH of 5.5 with citric acid was sprayed from the side onto 200.0 g of the particles coated with a middle layer obtained in Working Example 17 at a product temperature of 25° C., liquid feed rate of 6.0 g/min, and a spraying air pressure of 0.20 MPa using a fluidized bed granulator. The product was then treated under controlled temperature and humidity to obtain particles coated with a middle layer and a layer for controlling water penetration. The average particle diameter of the resulting particles coated with a middle layer and a layer for controlling water penetration was 246 μm.

Preparation of Fast-disintegrating Tablets Containing Particles Coated with Middle Layer and Layer for Controlling Water Penetration A mixture of 450.0 g of mannitol pulverized with a pin mill and sifted with a 42 mesh sieve and 90.0 g of the above-mentioned particles coated with a middle layer and a layer for controlling water penetration was granulated with 200.0 g of an aqueous solution containing 60.0 g of maltose to obtain granulated particles for fast-disintegrating tablets.

2.0 mg of magnesium stearate were mixed with 388.7 mg of the above-mentioned granulated particles, the mixture was filled into a die with a diameter of 10.5 mm, and the mixture was tableted at a pressure of 2.0 kN using an autograph to make tablets. These tablets were stored for 18 hours at 25° C. (relative humidity of 65%) and then for 3 hours at 30° C. (relative humidity of 40%) using a thermostatic constant-humidity chamber to make fast-disintegrating tablets. These fast-disintegrating tablets disintegrated in the oral cavity in 16 seconds.

Working Example 19

Preparation of Core Particles Containing a Drug

A liquid of 333.3 g of solifenacin succinate and 111.1 g of macrogol 6000 dissolved in a mixture of 552.6 g of methanol and 552.6 g of purified water was sprayed from the side onto 555.6 g of microcrystalline cellulose spheres at a product temperature of 45° C., liquid feed rate of 6.8 g/min, and spraying air pressure of 3.0 kg/cm$^2$ using a fluidized bed granulator to obtain core particles containing a drug. A liquid of 45.0 g of hydroxypropylmethylcellulose 2910 dissolved in a mixture of 427.5 g of methanol and 427.5 g of purified water was sprayed from the side onto 900.0 g of the resulting particles at a product temperature of 38° C., liquid feed rate of 6.0 g/min, and spraying air pressure of 0.28 MPa using a fluidized bed granulator.

Preparation of Particles Coated with Middle Layer

A coating liquid of 134.7 g of dibasic sodium citrate sesquihydrate (Kanto Kagaku, the same hereafter) and 24.2 g of hydroxypropylmethylcellulose 2910 dissolved in 1452.2 g of purified water was sprayed from the side onto 290.0 g of the resulting particles at a product temperature of 44° C., liquid feed rate of 6.0 g/min, and spraying air pressure, of 3.0 kg/cm$^2$ using a fluidized bed granulator to obtain particles coated with a middle layer.

Preparation of Particles Coated with Middle Layer and Layer for Controlling Water Penetration A liquid of 31.5 g of hydroxypropylmethylcellulose 2910 dissolved in a mixture of 299.3 g of methanol and 299.3 g of purified water was sprayed from the side onto 210.0 g of the above-mentioned particles coated with a middle layer at a product temperature of 43° C., liquid feed rate of 6.2 g/min, and spraying air pressure of 0.28 MPa using a fluidized bed granulator. A coating liquid obtained by dissolving 1.1 g of triethyl citrate and 11.3 g of aminoalkyl methacrylate copolymer RS in 342.0 g of methanol and adding 5.6 g of talc was sprayed from the side onto 200.0 g of the resulting particles at a product temperature of 28° C., liquid feed rate of 6.0 g/min, and spraying air pressure of 0.22 MPa using a fluidized bed granulator. A coating liquid obtained by dissolving 10.9 g of hydroxypropylmethylcellulose 2910 in 328.1 g of purified water and adding 72.9 g of an ethyl acrylate-methyl methacrylate copolymer dispersion and 36.5 g of ethylcellulose aqueous dispersion (FMC; Aquacoat ECD 30, the same hereafter) was sprayed from the side onto 175.0 g of the resulting particles at a product temperature of 30° C., liquid feed rate of 6.0 g/min, and air pressure of 0.25 MPa to obtain particles coated with a middle layer and a layer for controlling water penetration. The average particle diameter of the resulting particles coated with a middle layer and a layer for controlling water penetration was 240 μm.

Preparation of Fast-disintegrating Tablets Containing Particles Coated with Middle Layer and Layer for Controlling Water Penetration A mixture of 450.0 g of mannitol pulverized with a pin mill and sifted with a 42 mesh sieve and 90.0 g of the above-mentioned particles coated with a middle layer and a layer for controlling water penetration was granulated with 200.0 g of an aqueous solution containing 60.0 g of maltose to obtain granulated particles for fast-disintegrating tablets.

2.5 mg of magnesium stearate were mixed with 506.8 mg of the above-mentioned granulated particles, the mixture was filled into a die with a diameter of 12 mm, and the mixture was tableted at a pressure of 2.0 kN using an autograph to make tablets. These tablets were stored for 18 hours at 25° C. (relative humidity of 65%) and then for 3 hours at 30° C. (relative humidity of 40%) using a thermostatic constant-humidity chamber to make fast-disintegrating tablets. These fast-disintegrating tablets disintegrated in the oral cavity in 21 seconds.

Working Example 20

Preparation of Particles Coated with Middle Layer and Layer for Controlling Water Penetration A liquid of 30.0 g of hydroxypropylmethylcellulose 2910 dissolved in a mixture of 285.0 g of methanol and 285.0 g of purified water was sprayed from the side onto 200.0 g of the particles coated with a middle layer obtained in Working Example 19 at a product temperature of 38° C., liquid feed rate of 6.0 g/min, and spraying air pressure of 0.20 MPa using a fluidized bed granulator. A coating liquid obtained by dissolving 31.5 g of ethylcellulose and 10.5 g of hydroxypropylcellulose dissolved in 798.0 g of methanol was sprayed from the side onto 210.0 g of the resulting particles at a product temperature of 37° C., liquid feed rate of 5.0 g/min, and spraying air pressure of 2.5 kg/cm$^2$ using a fluidized bed granulator. A coating liquid obtained by dissolving 10.9 g of hydroxypropylmethylcellulose 2910 in 328.1 g of purified water and adding 72.9 g of an ethyl acrylate-methyl methacrylate copolymer dispersion and 36.5 g of an ethylcellulose aqueous dispersion was sprayed from the side onto 175.0 g of the resulting particles at a product temperature of 35° C., liquid feed rate of 6.0 g/min, and air pressure of 3.0 kg/cm$^2$ to obtain particles coated with a middle layer and a layer for controlling water penetration. The average particle diameter of the resulting particles coated with a middle layer and a layer for controlling water penetration was 275 μm.

Preparation of Fast-disintegrating Tablets Containing Particles Coated with Middle Layer and Layer for Controlling Water Penetration A mixture of 450.0 g of mannitol pulverized with a pin mill and sifted with a 42 mesh sieve and 90.0 g of the above-mentioned particles coated with a middle layer and a layer for controlling water penetration was granulated with 200.0 g of an aqueous solution containing 60.0 g of maltose to obtain granulated particles for fast-disintegrating tablets.

2.8 mg of magnesium stearate were mixed with 558.0 mg of the above-mentioned granulated particles, the mixture was filled into a die with a diameter of 16 mm, and the mixture was tableted at a pressure of 2.0 kN using an autograph to make tablets. These tablets were stored for 18 hours at 25° C. (relative humidity of 65%) and then for 3 hours at 30° C. (relative humidity of 40%) using a thermostatic constant-humidity chamber to make fast-disintegrating tablets. These fast-disintegrating tablets disintegrated in the oral cavity in 20 seconds.

Working Example 21

Preparation of Core Particles Containing a Drug

A liquid of 300.0 g of diphenhydramine hydrochloride (Kongo Chemical Co., Ltd.) and 60.0 g of hydroxypropylmethylcellulose 2910 dissolved in a mixture of 720.0 g of methanol and 720.0 g of purified water was sprayed from the side onto 600.0 g of microcrystalline cellulose spheres (Asahi Kasei Chemicals Corporation; SCP-100) at a product temperature of 38° C., liquid feed rate of 10.0 g/min, and spraying air pressure of 3.0 kg/cm$^2$ using a fluidized bed granulator to obtain core particles containing a drug. A liquid of 20.0 g of hydroxypropylmethylcellulose 2910 dissolved in a mixture of 190.0 g of methanol and 190.0 g of purified water was sprayed from the side onto 400.0 g of the resulting particles at a product temperature of 40° C., liquid feed rate of 6.0 g/min, and spraying air pressure of 3.0 kg/cm$^2$ using a fluidized bed granulator.

Preparation of Particles Coated with Middle Layer

A coating liquid of 134.7 g of dibasic sodium citrate sesquihydrate and 24.2 g of hydroxypropylmethylcellulose 2910 dissolved in 1452.2 g of purified water was sprayed from the side onto 290.0 g of the resulting particles at a product temperature of 46° C., liquid feed rate of 7.0 g/min, and spraying air pressure of 3.0 kg/cm$^2$ using a fluidized bed granulator to obtain particles coated with a middle layer.

Preparation of Particles Coated with Middle Layer and Layer for Controlling Water Penetration A liquid of 18.0 g of hydroxypropylmethylcellulose 2910 dissolved in a mixture of 171.0 g of methanol and 171.0 g of purified water was sprayed from the side onto 360.0 g of the above-mentioned particles coated with a middle layer at a product temperature of 40° C., liquid feed rate of 5.0 g/min, and spraying air pressure of 3.0 kg/cm$^2$ using a fluidized bed granulator. A coating liquid obtained by dissolving 1.1 g of triethyl citrate and 11.5 g of aminoalkyl methacrylate copolymer RS in 348.8 g of methanol and adding 5.7 g of talc was sprayed from the side onto 200.0 g of the resulting particles at a product temperature of 30° C., liquid feed rate of 5.0 g/min, and spraying air pressure of 2.5 kg/cm$^2$ using a fluidized bed granulator. A coating liquid obtained by dissolving 14.1 g of hydroxypropylmethylcellulose 2910 in 409.3 g of purified water and adding 94.1 g of an ethyl acrylate-methyl methacrylate copolymer dispersion and 47.0 g of an ethylcellulose aqueous dispersion was sprayed from the side onto 130.0 g of the resulting particles at a product temperature of 40° C., liquid feed rate of 5.0 g/min, and air pressure of 3.0 kg/cm$^2$ to obtain particles coated with a middle layer and a layer for controlling water penetration. The average particle diameter of the resulting particles coated with a middle layer and a layer for controlling water penetration was 205 μm.

Preparation of Fast-disintegrating Tablets Containing Particles Coated with Middle Layer and Layer for Controlling Water Penetration A mixture of 450.0 g of mannitol pulverized with a pin mill and sifted with a 42 mesh sieve and 90.0 g of the above-mentioned particles coated with a middle layer and a layer for controlling water penetration was granulated with 200.0 g of an aqueous solution containing 60.0 g of maltose to obtain granulated particles for fast-disintegrating tablets.

7.1 mg of magnesium stearate were mixed with 1417.9 mg of the above-mentioned granulated particles, the mixture was filled into a die with a diameter of 16 mm, and the mixture was tableted at a pressure of 2.0 kN using an autograph to make tablets. These tablets were stored for 18 hours at 25° C. (relative humidity of 65%) and then for 3 hours at 30° C. (relative humidity of 40%) using a thermostatic constant-humidity chamber to make fast-disintegrating tablets. These fast-disintegrating tablets disintegrated in the oral cavity in 32 seconds.

Working Example 22

Preparation of Middle Layer Coating Liquid 79.5 g of citric acid monohydrate (Kanto Kagaku) were dissolved in 450.5 g of purified water and 265.0 g of methacrylic acid copolymer LD (Rohm; Eudragit L30D-55) were added and agitated to prepare a middle layer coating liquid.

Preparation of Particles Coated with Middle Layer

The above-mentioned middle layer coating liquid was sprayed from the side onto 300.0 g of the core particles containing a drug obtained in Working Example 1 at a product temperature of 32° C., liquid feed rate of 6.0 g/min, and spraying air pressure of 0.24 MPa using a fluidized bed granulator to obtain particles coated with a middle layer that had been coated with 53 wt % of a middle layer in terms of the core particles containing a drug. The average particle diameter of the resulting particles coated with a middle layer was 760 μm.

Preparation of Coating Liquid for Layer for Controlling Water Penetration 24.0 g of cetanol were dissolved in 456.0 g of methylene chloride to prepare the coating liquid for a layer for controlling water penetration.

Preparation of Particles Coated with Middle Layer and Layer for Controlling Water Penetration The above-mentioned coating liquid for the layer for controlling water penetration was sprayed from the side onto 400.0 g of the particles coated with a middle layer at a product temperature of 30° C., liquid feed rate of 10.6 g/min, and a spraying air pressure of 0.15 MPa using a fluidized bed granulator to obtain particles coated with a middle layer and a layer for controlling water penetration wherein particles coated with a middle layer had been coated with 6 wt % of a layer for controlling water penetration. The average particle diameter of the resulting particles coated with a middle layer and a layer for controlling water penetration was 764 μm.

Working Example 23

Preparation of Middle Layer Coating Liquid 103.3 g of dibasic sodium phosphate dihydrate and 79.5 g of hydroxypropylmethylcellulose acetate succinate (Shin-Etsu Chemical Co., Ltd.; Shin-Etsu AQOAT AS-LF) were added to 1590.0 g of purified water and agitated to prepare a middle layer coating liquid.

Preparation of Particles Coated with Middle Layer

The above-mentioned middle layer coating liquid was sprayed from the side onto 300.0 g of the core particles containing a drug obtained in Working Example 1 at a product temperature of 31° C., liquid feed rate of 6.2 g/min, and spraying air pressure of 0.25 MPa using a fluidized bed granulator to obtain particles coated with a middle layer wherein core particles containing a drug had been coated with 53 wt % of a middle layer. The average particle diameter of the resulting particles coated with a middle layer was 758 μm.

Preparation of Coating Liquid for Layer for Controlling Water Penetration 20.0 g of cetanol were dissolved in 380.0 g of methylene chloride to prepare the coating liquid for a layer for controlling water penetration.

Preparation of Particles Coated with Middle Layer and Layer for Controlling Water Penetration The above-mentioned coating liquid for the layer for controlling water penetration was sprayed from the side onto 400.0 g of the particles coated with a middle layer at a product temperature of 31° C., liquid feed rate of 10.2 g/min, and spraying air pressure of 0.15 MPa using a fluidized bed granulator to obtain particles coated with a middle layer and a layer for controlling water penetration wherein particles coated with a middle layer had been coated with 5 wt % of a layer for controlling water penetration. The average particle diameter of the resulting particles coated with a middle layer and a layer for controlling water penetration was 764 μm.

Test Example 1

Dissolution Test on Pharmaceutical Composition in Particle Form

The particles coated with a middle layer and a layer for controlling water penetration obtained in Working Examples 1, 2, 3, 4, 5, 6, 7, 8 and 22, the particles coated with an insolubilizing substance layer obtained in Comparative Example 1, the particles coated with a middle layer obtained in Comparative Example 2, the particles coated with an insolubilizer layer and a layer for controlling water penetration obtained in Comparative Example 3, and the particles coated with an insolubilizing substance layer and a layer for controlling water penetration obtained in Comparative Example 4, each containing 10 mg of acetaminophen, were weighed and dissolution tests were conducted in accordance with Dissolution Test Method 2 (Paddle method) cited in The Japanese Pharmacopeia fourteenth edition using an automatic 6-series dissolution testing device (Toyama Sangyo Co., Ltd.). Moreover, the particles coated with a layer for controlling water penetration obtained in Comparative Examples 5 and 6 and the particles coated with a middle layer and a layer for controlling water penetration obtained in Working Examples 9 and 10, each containing 20 mg of imipramine hydrochloride, were weighed and dissolution tests were similarly conducted. The test fluid was 500 mL of phosphate buffer with a pH of 6.8 (2nd fluid identified in Disintegration Test cited in The Japanese Pharmacopeia fourteenth edition). The number of revolutions of the paddles was 100 revolutions per minute. The particles coated with a middle layer and a layer for controlling water penetration containing 5 mg of solifenacin succinate obtained in Working Examples 14, 15, 16, 17, 18, and 20, and the particles coated with a middle layer and a layer for controlling water penetration containing 50 mg of diphenhydramine hydrochloride obtained in Working Example 21 were weighed out and dissolution tests were similarly conducted. The test fluid was 900 mL of phosphate buffer with a pH of 6.8 (2nd fluid identified in Disintegration Test cited in The Japanese Pharmacopeia fourteenth edition). The paddle number of revolutions was 100 rpm/minute. The dissolution profiles obtained from the results of the tests are shown in FIGS. 1 through 18.

*International Journal of Pharmaceutics*, 241, 113-125 (2002), and *International Journal of Pharmaceutics*, 273, 109-119 (2004). In contrast to this, a lag time of approximately four minutes formed with the particles prepared in Working Example 2. This indicates that not only a layer composed of insolubilizer and insolubilizing substance, but also the layer for controlling water penetration are essential for formation of lag time with pharmaceutical compositions in particle form.

[FIG. 2]

The particles prepared in Comparative Examples 3 and 4 are core particles containing a drug coated with only one of the components that make up the middle layer of the present invention and further, a layer for controlling water penetration. The particles prepared by Comparative Example 3 contain only an insolubilizer (sodium carbonate) between a core particle containing a drug and a layer for controlling water penetration, and a lag time is not formed. Moreover, the particles prepared by Comparative Example 4 contain only an insolubilizing substance (hydroxypropylmethylcellulose) between a core particle containing a drug and a layer for controlling water penetration, and a lag time is not formed. On the other hand, the particles coated with a middle layer and

TABLE 1

Results of dissolution tests on particles coated with middle layer and particles coated with a middle layer and a layer for controlling water penetration

|  |  | Working Example 1 | Working Example 2 | Working Example 8 | Working Example 9 | Working Example 10 |  |
| --- | --- | --- | --- | --- | --- | --- | --- |
| Dissolution rate (%) | 1 min. | 0.0 | 0.0 | 0.0 | 0.0 | 0.0 |  |
|  | 3 mins. | 0.0 | 0.3 | 0.0 | 0.0 | 0.2 |  |
|  | 60 mins. | 99.2 | 99.5 | 96.1 | 99.0 | 95.9 |  |
|  |  | Comparative Example 1 | Comparative Example 2 | Comparative Example 3 | Comparative Example 4 | Comparative Example 5 | Comparative Example 6 |
| Dissolution rate (%) | 11 min. | 10.3 | 9.9 | 15.3 | 16.4 | 3.3 | 1.4 |
|  | 3 mins. | 94.9 | 53.0 | 59.8 | 41.1 | 32.3 | 18.0 |
|  | 60 mins. | 99.7 | 99.8 | 99.7 | 99.4 | 90.5 | 86.0 |

[FIG. 1]

The particles coated with an insolubilizing substance layer prepared in Comparative Example 1 are particles obtained by coating core particles containing a drug with 53 wt % of a salting out-type insolubilizing substance (hydroxypropylmethylcellulose) only. They are not coated with a layer for controlling water penetration, and lag time is not formed. This indicates that because the surface area that contacts water is large and the speed of water penetration and drug release is fast with pharmaceutical compositions in particle form that are small in size and have a thin coating layer, the layer of water-soluble polymer cannot suppress the drug dissolution speed. Moreover, the particles coated with a middle layer prepared in Comparative Example 2 are coated with 53 wt % of a layer composed of an insolubilizer (sodium carbonate) and insolubilizing substance (hydroxypropylmethylcellulose). They are not coated with a layer for controlling water penetration, and the desired lag time is not obtained. This indicates that because the speed of water penetration and drug release is fast with pharmaceutical compositions in particle form, it is impossible to form lag time via insolubilization simply by coating the particles with a layer composed of an insolubilizer and an insolubilizing substance. These findings indicate that this phenomenon is not the same as the phenomenon that is seen with tablets having a large diameter cited in a layer for controlling water penetration prepared in Working Example 2 form a sufficient lag time, indicating that it is essential for the formation of lag time that the middle layer contain both an insolubilizer and an insolubilizing substance. Moreover it shows that the present invention and the reference *Journal of Controlled Release*, 89, 47-55 (2003) are completely different in terms of technological concept, and the added components and the function of the layers. In other words, the purpose of the tablets in this reference containing both sodium chloride, which is the equivalent of the insolubilizer of the present invention, and hydroxypropylmethylcellulose, which is the equivalent of the insolubilizing substance of the present invention, is fast release of the drug, and this is clearly different from the present invention in terms of structure and concept.

[FIG. 3]

The particles coated with a layer for controlling water penetration prepared in Comparative Examples 5 and 6 are core particles containing a drug coated with 7 wt % or 10 wt % of a layer for controlling water penetration composed of a water-insoluble polymer and a water-soluble polymer. The particles prepared in Comparative Example 5 release 90% or more of the drug in 60 minutes, but do not form a lag time of two minutes or longer. The particles prepared in Comparative Example 6 do not form a lag time of two minutes or longer or release 90% or more of the drug in 60 minutes. Thus, it is impossible to both realize a lag time of two minutes or longer and obtain fast drug release when core particles are coated with a layer for controlling water penetration to a predetermined amount of coating between 7 and 10%. In short, the objectives of the present invention cannot be accomplished by coating core particles containing a drug with only a layer for controlling water penetration. In contrast to this, the particles prepared in Working Example 9 have already released 90% or more of the drug 27 minutes after starting the dissolution test following a lag time of approximately four minutes. A sufficient lag time can be formed and fast drug release is possible with these particles.

[FIG. 4]

The particles coated with a middle layer and a layer for controlling water penetration obtained in Working Examples 1, 2, and 8 each release a drug quickly after a lag time of two minutes or longer. The particles prepared in Working Example 1 are core particles containing a drug coated with 53 wt % of a middle layer and further, 8 wt % of a layer for controlling water penetration, and form a lag time of approximately eight minutes. The particles prepared in Working Example 2 are core particles containing a drug coated with 53 wt % of a middle layer and 5 wt % of a layer for controlling water penetration, and form a lag time of approximately four minutes. This indicates that it is possible to maintain fast drug release and control lag time with the pharmaceutical composition in particle form of the present invention by adjusting the amount of coating with the layer for controlling water penetration. The particles prepared in Working Example 8 are core particles containing a drug coated with 72 wt % of a middle layer and 5 wt % of a layer for controlling water penetration, and form a lag time of approximately 12 minutes. This finding indicates that when compared to Working Example 2, it is possible to realize not only fast drug release but also control of lag time with the pharmaceutical composition in particle form of the present invention by adjusting the amount of coating with the middle layer. In other words, it indicates that the lag time can be controlled as needed with the pharmaceutical composition in particle form obtained by the present invention by adjusting the amount of coating with the middle layer and the layer for controlling water penetration.

[FIG. 5]

The particles obtained in Working Examples 9 and 10 are particles obtained by coating microcrystalline cellulose spheres with a drug and further coating the product with a middle layer and a layer for controlling water penetration. Both of these particles release the drug quickly after a lag time of two minutes or longer. The particles prepared in Working Example 9 are obtained by coating particles coated with a middle layer with 4 wt % of a layer for controlling water penetration, and formed a lag time of approximately four minutes. The particles prepared in Working Example 10 are obtained by coating particles coated with a middle layer with 7 wt % of a layer for controlling water penetration, and form a lag time of approximately ten minutes. This indicates that the lag time that is produced with the pharmaceutical composition in particle form obtained by the present invention can also be controlled as needed by adjusting the amount of coating of layer for controlling water penetration alone, even if the composition is a pharmaceutical composition in particle form with a particle diameter of 300 μm or smaller that produces little gritty sensation when used in fast-disintegrating tablets.

[FIGS. 6, 7, 8, 9, and 10]

90% or more of the drug was released 60 minutes after starting the dissolution tests after a lag time of two or more minutes in each case from the particles coated with a middle layer and a layer for controlling water penetration obtained in Working Examples 3, 4, 5, 6, and 7. The dibasic sodium phosphate dihydrate, trisodium citrate dihydrate, sodium chloride, glycine, and sucrose used as salting out-type insolubilizers in Working Examples 3, 4, 5, 6, and 7 all had a $\Delta CST_1$ of 10° C. or higher. This finding indicates that suppression of early drug dissolution and quick drug release following a lag time are possible, regardless of the material used as long as it has the specific property values specified in the present Specificaiton for insolubilizers.

[FIGS. 11, 12, 13, and 14]

90% or more of the drug was released 60 minutes after starting the dissolution tests after a lag time of two or more minutes in each case from the particles coated with a middle layer and layer for controlling water penetration that were obtained in Working Examples 14, 15, 16, and 17. The polyvinyl alcohol-polyethylene glycol graft copolymer, hydroxypropylcellulose, partially hydrolyzed polyvinyl alcohol, and methylcellulose used as the salting out-type insolubilizing substance in Working Examples 14, 15, 16, and 17, respectively, all had a $CST_2$ of 55° C. or lower and a $CST_3$ of 37° C. or higher. These findings indicate that suppression of early drug dissolution and quick drug release following a lag time are possible regardless of the substance used as long as it has the specific property values specified in the present Specificaiton for insolubilizing substances.

Figure 14:
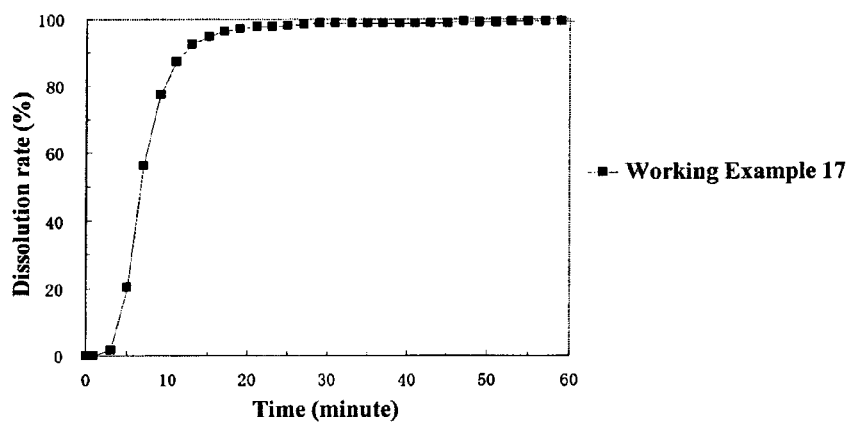
FIG. 14 shows the dissolution profiles obtained by dissolution tests of the pharmaceutical composition in particle form of Working Example 17.
Figure 15:
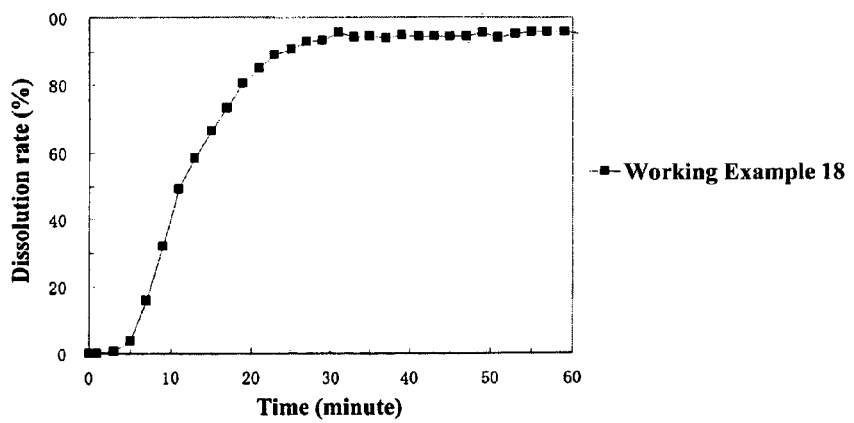
FIG. 15 shows the dissolution profiles obtained by dissolution tests of the pharmaceutical composition in particle form of Working Example 18.
Figure 16:
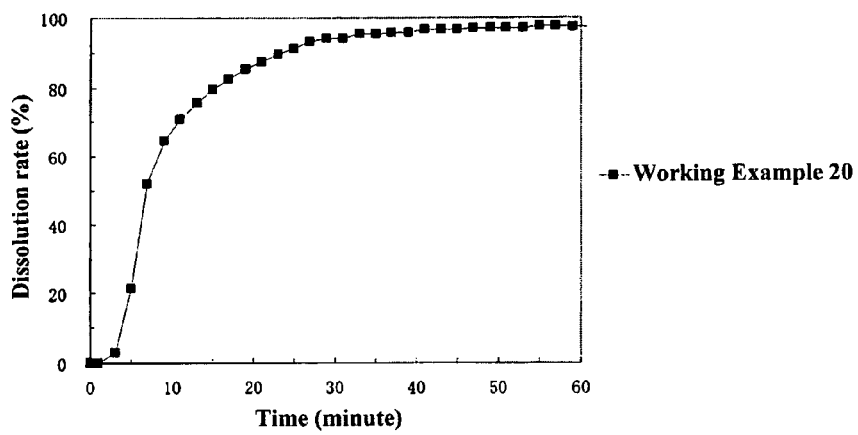
FIG. 16 shows the dissolution profiles obtained by dissolution tests of the pharmaceutical composition in particle form of Working Example 20.
Figure 17:
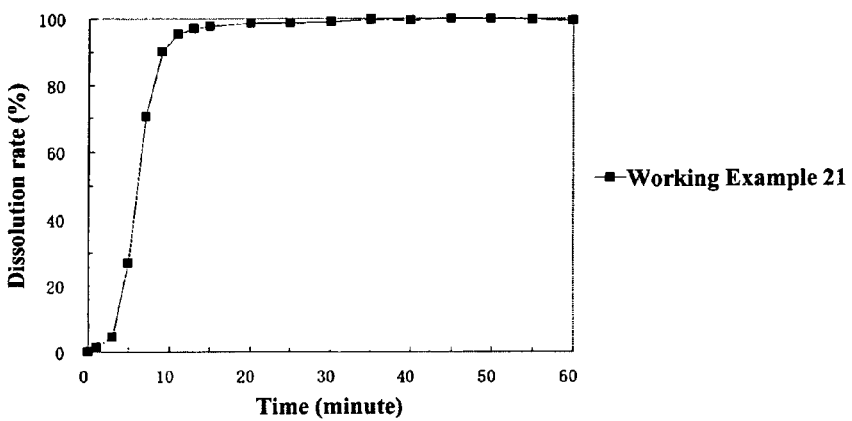
FIG. 17 shows the dissolution profiles obtained by dissolution tests of the pharmaceutical composition in particle form of Working Example 21.
Figure 18:
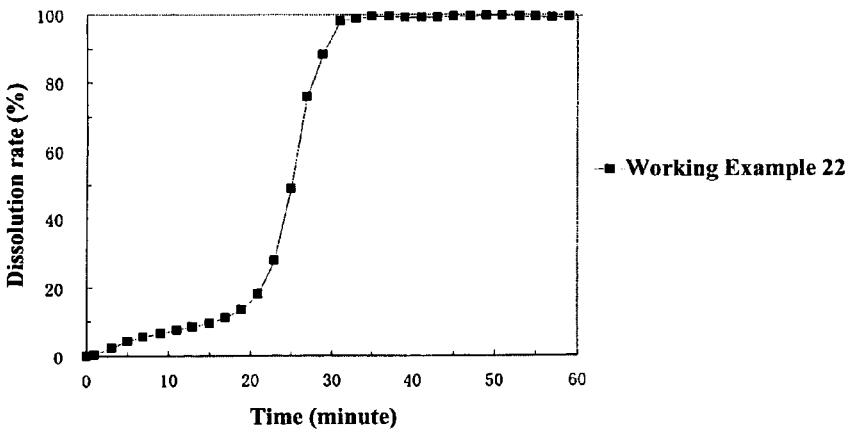
FIG. 18 shows the dissolution profiles obtained by dissolution tests of the pharmaceutical composition in particle form of Working Example 22.

[FIGS. 14, 15, and 16]

90% or more of the drug was released 60 minutes after starting the dissolution tests after a lag time of two or more minutes in each case from the particles coated with a middle layer and layer for controlling water penetration that were obtained in Working Examples 17, 18, and 20. The polyvinyl acetate dispersion stabilized with povidone and sodium lauryl sulfate/triethyl citrate/talc, ammonio methacrylate copolymer dispersion, type B/ethyl acrylate-methyl methacrylate copolymer dispersion/polysorbate 80, and ethylcellulose/hydroxypropylcellulose/ethyl acrylate-methyl methacrylate copolymer dispersion ethylcellulose aqueous dispersion/hydroxypropylmethylcellulose 2910 used for the layer for controlling water penetration in Working Examples 17, 18, and 20 all contained one or more water-insoluble substance and one or more water-soluble substance. These findings indicate that that suppression of early drug dissolution and quick drug release following a lag time are possible regardless of the substances and combinations used as long as they have the specific property values specified in the present Specificaiton for the layer for controlling water penetration.

[FIGS. 4, 5, 14, and 17]

90% or more of the drug was released 60 minutes after starting the dissolution tests after a lag time of two or more minutes in each case from the particles coated with a middle layer and layer for controlling water penetration that were obtained in Working Examples 1, 9, 17, and 21. Acetaminophen, imipramine hydrochloride, solifenacin succinate, and diphenhydramine hydrochloride were used as the drug in Working Examples 1, 9, 17, and 21, respectively. By means of the present invention, it is possible to control lag time in accordance with the properties of the drug and these findings therefore indicate that suppression of early drug dissolution and quick drug release following a lag time are possible regardless of the type or properties of the drug.

[FIG. 18]

The middle layer of the particles coated with a middle layer and layer for controlling water penetration that were obtained in Working Example 22 contained citric acid monohydrate, which is an acid-type insolubilizer, and methacrylic acid copolymer LD, which is an acid-type insolubilizing substance, and 90% or more of the drug was released 60 minutes after starting the dissolution tests after a lag time of two or more minutes. On the other hand, the fact that the middle layer in Working Examples 1 through 21 contained a salting out-type insolubilizer and salting out-type insolubilizing substance contributed to both suppression of early drug dissolution and fast drug release after a lag time. Taking these points into consideration, it is possible to simultaneously accomplish suppression of early drug dissolution and fast drug release after a lag time, regardless of the theory behind the insolubilization, as long as the insolublizer and insolubilizing substance are both water soluble and the insolublizer has the ability to insolubilize the insolubilizing substance.

[Dissolution Profile of Fast-disintegrating Tablets Containing Particles Coated with Middle Layer and Layer for Controlling Water Penetration Obtained in Working Examples 11, 17, 18, 19, 20, and 21]

The dissolution profile of the fast-disintegrating tablets containing particles coated with a middle layer and a layer for controlling water penetration that were obtained in Working Examples 11, 17, 18, 19, 20, and 21 coincided with the dissolution profile of particles coated with middle layer and layer for controlling water penetration obtained in Working Examples 11, 17, 18, 19, 20, and 21.

Test Example 2

Sensory Tests

Sensory tests were conducted using 50 mg of imipramine hydrochloride (Table 2). Sensory tests were conducted using particles coated with a middle layer and a layer for controlling water penetration obtained in Working Example 9 that contained 50 mg of imipramine hydrochloride (Table 3). The sensory tests were conducted by three healthy adults who kept the imipramine hydrochloride or the particles coated with a middle layer and layer for controlling water penetration in the oral cavity for one minute, swallowed, and evaluated the bitter taste and astringent taste for seven minutes without drinking water or gargling.

TABLE 2

Results of sensory tests with imipramine hydrochloride

| After administration | Bitter taste Tester | | | Astringent taste Tester | | |
|---|---|---|---|---|---|---|
| | No.1 | No.2 | No.3 | No.1 | No.2 | No.3 |
| 1 minute | ± | ± | + | − | ± | + |
| 3 minutes | + | + | ± | + | + | + |
| 5 minutes | − | − | − | + | + | + |
| 7 minutes | − | − | − | ++ | + | + |

TABLE 3

Results of sensory tests with particles coated with a middle layer and a layer for controlling water penetration

| After administration | Bitter taste Tester | | | Astringent taste Tester | | |
|---|---|---|---|---|---|---|
| | No.1 | No.2 | No.3 | No.1 | No.2 | No.3 |
| 1 minute | − | − | − | − | − | − |
| 1 minute | − | − | − | − | − | − |
| 3 minutes | − | − | − | − | − | − |
| 5 minutes | − | − | − | − | − | − |
| 7 minutes | − | − | − | − | − | − |

Evaluation of unpleasant taste: − (Did not notice an unpleasant taste); ± (noticed a slight change in taste, but it could be tolerated), + (noticed an unpleasant taste), ++ (noticed a strong unpleasant taste)

As shown in Table 2, imipramine hydrochloride is a drug with a bitter and very astringent taste and it retains this astringent taste for a long time. However, as shown in Table 3, the bitter and astringent taste of the particles obtained in Working Example 9 can be completely masked, and it is clear that the unpleasant taste of a drug can be masked as a result of controlling drug release for a specific time by means of the pharmaceutical composition in particle form of the present invention.

INDUSTRIAL APPLICABILITY

The present invention relates to a pharmaceutical composition in particle form for oral use, which can be obtained by coating core particles containing a drug with (1) a middle layer containing two types of water-soluble components, an insolubilizer and an insolubilizing substance, and further (2) a layer for controlling water penetration containing a water-insoluble substance, and fast-disintegrating tablets containing this composition. The present invention makes it possible to (A) suppress drug release for a predetermined time (lag time hereafter), (B) quickly release the drug after a lag time, and (C) control the length of the lag time as needed. Drug release in the oral cavity is suppressed by suppressing drug release for a pre-determined time; therefore, the unpleasant feeling from a drug with an unpleasant taste is alleviated and compliance can be improved. Moreover, it is possible to avoid problems such as an increase in individual differences in adverse events and pharmacological effects that is absorbed in the oral cavity. The drug is released in the upper gastrointestinal tract because it is quickly released after a lag time and sufficient pharmacological effects can therefore be realized. The length of the lag time can be controlled in accordance with the properties of the drug or pharmaceutical preparation by controlling as needed the length of the lag time; as a result, the present invention can be used for drugs having a wide range of properties and pharmaceutical preparations having a wide range of characteristics.

The invention claimed is:

1. An oral timed-release pharmaceutical composition in particle form, which comprises particles, wherein each particle has an average diameter of 1 to 350 μm, comprising:
   a) a drug at the core, wherein the core is not pre-coated;
   b) a middle layer that contains two types of water-soluble components, wherein the components comprise:
      i) an insolubilizer, which is a salting out-type insolubilizer that is one or more selected from the group consisting of sodium carbonate, monobasic sodium phosphate, dibasic sodium phosphate, sodium metaphosphate, trisodium phosphate, potassium bicarbonate, sodium bicarbonate, sodium polyphosphate, sodium pyrophosphate, sodium chloride, potassium chloride, sodium sulfate, sodium sulfite, sodium citrate, dibasic sodium citrate, monosodium glutamate, disodium succinate, glycine, alanine, sorbitol, xylitol, inositol, sucrose, glucose, and fructose; and ii) an insolubilizing substance, which is a salting out-type insolubilizing substance that is one or more selected from the group consisting of hydroxypropylmethylcellulose, hydroxypropylcellulose, methylcellulose, polyvinyl alcohol-polyethylene glycol graft copolymer, carboxyvinyl polymer, polyvinyl alcohol, polyethylene oxide, povidone, copolyvidone, polyoxyethylene hydrogenated castor oil, polymers containing isopropylacrylamide and derivatives where hydrophobic groups have been introduced to the N position of acrylamide, and polyoxyethylene polyoxypropylene glycol;

wherein the range of insolubilizer in terms of the weight of the middle layer is 20 wt % or greater but less than 95 wt %, the drug core is directly coated with the middle layer, wherein the middle layer is optionally precoated with one or more coating layers; and c) an outer layer for controlling water penetration speed that contains a water-insoluble substance, wherein said composition has a lag time within a length of 2 to 20 minutes and then the drug is quickly released, wherein the composition is in a form of a fast-disintegrating tablet and wherein the ratio of the outer layer to core containing drug is 7.7 to 17.5% wt.

2. A taste-masked oral pharmaceutical composition in particle form, which comprises particles, wherein each particle has an average diameter of 1 to 350 μm, comprising:

a) a drug at the core, wherein the core is not pre-coated;

b) a middle layer that contains two types of water-soluble components, wherein the components comprise:

i) an insolubilizer, which is a salting out-type insolubilizer that is one or more selected from the group consisting of sodium carbonate, monobasic sodium phosphate, dibasic sodium phosphate, sodium metaphosphate, trisodium phosphate, potassium bicarbonate, sodium bicarbonate, sodium polyphosphate, sodium pyrophosphate, sodium chloride, potassium chloride, sodium sulfate, sodium sulfite, sodium citrate, dibasic sodium citrate, monosodium glutamate, disodium succinate, glycine, alanine, sorbitol, xylitol, inositol, sucrose, glucose, and fructose; and ii) an insolubilizing substance, which is a salting out-type insolubilizing substance that is one or more selected from the group consisting of hydroxypropylmethylcellulose, hydroxypropylcellulose, methylcellulose, polyvinyl alcohol-polyethylene glycol graft copolymer, carboxyvinyl polymer, polyvinyl alcohol, polyethylene oxide, povidone, copolyvidone, polyoxyethylene hydrogenated castor oil, polymers containing N-isopropylacrylamide and derivatives where hydrophobic groups have been introduced to the N position of acrylamide, and polyoxyethylene polyoxypropylene glycol, wherein the range of insolubilizer in terms of the weight of the middle layer is 20 wt % or greater but less than 95 wt %, the drug core is directly coated with the middle layer, wherein the middle layer is optionally precoated with one or more coating layers; and c) an outer layer for controlling water penetration speed that contains a water-insoluble substance, wherein said composition has a lag time within a length of 2 to 20 minutes and then the drug is quickly released, wherein the composition is in a form of a fast-disintegrating tablet and wherein the ratio of the outer layer to core containing drug is 7.7 to 17.5% wt.

3. The pharmaceutical composition in particle form according to claim 1, where the salting out-type insolubilizer is one or more selected from the group of substances consisting of sodium carbonate, monobasic sodium phosphate, dibasic sodium phosphate, sodium citrate, and dibasic sodium citrate.

4. The pharmaceutical composition in particle form according to claim 1, where the salting out-type insolubilizing substance is one or more selected from the group of substances consisting of hydroxypropylmethylcellulose, hydroxypropylcellulose, methylcellulose, polyvinyl alcohol-polyethylene glycol graft copolymer, polymers containing N-isopropylacrylamide and derivatives where hydrophobic groups have been introduced to the N position of acrylamide, and polyoxyethylene polyoxypropylene glycol.

5. The pharmaceutical composition in particle form according to claim 1, where the amount of coating of the middle layer is 1 to 500 wt % in terms of the weight per core containing drug.

6. The pharmaceutical composition in particle form according to claim 1, where the layer for controlling water penetration contains one or more water-insoluble substance and further, can contain one or more water-soluble substance.

7. The pharmaceutical composition in particle form according to claim 6, where the water-insoluble substance is one or more selected from the group consisting of ethylcellulose, celluloseacetate, polyvinyl acetate, celluloseacetate phthalate, carboxymethylethylcellulose, hydroxypropylmethylcellulose acetate succinate, hydroxypropylmethylcellulose phthalate, dimethylpolysiloxane, polydimethylsiloxane-silicon dioxide mixture, dimethylaminoethylmethacrylate-methylmethacrylate copolymer, methylacrylate-methacrylic acid copolymer, ethyl acrylate-methyl methacrylate copolymer emulsion, aminoalkyl methacrylate copolymer RS, dried methacrylic acid copolymer LD, aminoalkyl methacrylate copolymer E, methacrylic acid copolymer L, methacrylic acid copolymer LD, methacrylic acid copolymer S, polyvinylacetal diethylaminoacetate, casein, shellac, and zein.

8. The pharmaceutical composition in particle form according to claim 6, where the water-soluble substance is one or more selected from the group consisting of powdered acacia, sodium alginate, pregelatinized starch, sodium caseinate, carrageenan, carboxyvinyl polymer, sodium carboxymethyl starch, carmellose sodium, xanthan gum, sucrose esters of fatty acids, dextran, dextrin, lactose, hydroxypropylcellulose, hydroxypropylmethylcellulose, methylcellulose, hydroxyethylcellulose, pullulan, povidone, copolyvidone, polyoxyethylene hydrogenated castor oil, polyoxyethylene polyoxypropylene glycol, aminoalkyl methacrylate copolymer E, polyvinylacetal diethylaminoacetate, polyvinyl alcohol-polyethylene glycol graft copolymer, polyvinyl alcohol, macrogol, polyethylene oxide, glycine, alanine, aspartame, glycyrrhizinic acid, sucrose, fructose, maltose, glucose, cyclodextrin, mannitol, xylitol, maltitol, and sorbitol.

9. The pharmaceutical composition in particle form according to claim 1, where the drug contained in the particles is a drug that has an unpleasant taste.

10. The pharmaceutical composition in particle form according to claim 9, where the drug contained in the particles is solifenacin or a salt thereof, or diphenhydramine or a salt thereof.

11. The pharmaceutical composition in particle form according to claim 1, wherein said composition has a drug dissolution rate one hour after starting the dissolution test of 90 to 100% in tests using test fluid that simulates gastrointestinal fluid.

12. The pharmaceutical composition in particle form according to claim 1, wherein said composition further comprises a member selected from the group consisting of a binder, a disintegrating agent, a lubricant, a flavoring agent, a sweetener, a refrigerant, a fragrance, a coloring agent, a foaming agent, a stabilizer, an antioxidant, a preservative, and a filler.

13. The masked oral pharmaceutical composition in particle form according to claim 2, wherein said composition further comprises a member selected from the group consisting of a binder, a disintegrating agent, a lubricant, a flavoring agent, a sweetener, a refrigerant, a fragrance, a coloring agent, a foaming agent, a stabilizer, an antioxidant, a preservative, and a filler.

14. An oral timed-release pharmaceutical composition in particle form, which comprises particles, wherein each particle has an average diameter of 1 to 350 μm, comprising:
   a) a core consisting essentially of a drug and a precoat wherein said precoat is a hydroxypropylmethylcellulose (HPMC) coating, which will not prevent lag time formation nor fast drug release and thereafter coated with a middle layer;
   b) said middle layer contains two types of water-soluble components, wherein the components comprise:
      i) an insolubilizer, which is a salting out-type insolubilizer that is one or more selected from the group consisting of sodium carbonate, monobasic sodium phosphate, dibasic sodium phosphate, sodium metaphosphate, trisodium phosphate, potassium bicarbonate, sodium bicarbonate, sodium polyphosphate, sodium pyrophosphate, sodium chloride, potassium chloride, sodium sulfate, sodium sulfite, sodium citrate, dibasic sodium citrate, monosodium glutamate, disodium succinate, glycine, alanine, sorbitol, xylitol, inositol, sucrose, glucose, and fructose; and
      ii) an insolubilizing substance, which is a salting out-type insolubilizing substance that is one or more selected from the group consisting of hydroxypropylmethylcellulose, hydroxypropylcellulose, methylcellulose, polyvinyl alcohol-polyethylene glycol graft copolymer, carboxyvinyl polymer, polyvinyl alcohol, polyethylene oxide, povidone, copolyvidone, polyoxyethylene hydrogenated castor oil, polymers containing N-isopropylacrylamide and derivatives where hydrophobic groups have been introduced to the N position of acrylamide, and polyoxyethylene polyoxypropylene glycol, the range of insolubilizer in terms of the weight of the middle layer is 20 wt % or greater but less than 95 wt %;
   wherein the drug core is directly coated with the middle layer, wherein the middle layer is optionally precoated with one or more coating layers; and
   c) an outer layer for controlling water penetration speed that contains a water-insoluble substance, wherein said composition has a lag time within a length of 2 to 20 minutes and then the drug is quickly released, wherein the composition is in a form of a fast-disintegrating tablet.

15. An oral timed-release pharmaceutical composition in particle form, which comprises particles, wherein each particle has an average diameter of 1 to 350 μm, comprising:
   a) a core consisting essentially of a drug and a precoat, wherein said precoat is a povidone coating, which will not prevent lag time formation nor fast drug release, and thereafter coated with a middle layer;
   b) said middle layer contains two types of water-soluble components, wherein the components comprise:
      i) an insolubilizer, which is a salting out-type insolubilizer that is one or more selected from the group consisting of sodium carbonate, monobasic sodium phosphate, dibasic sodium phosphate, sodium metaphosphate, trisodium phosphate, potassium bicarbonate, sodium bicarbonate, sodium polyphosphate, sodium pyrophosphate, sodium chloride, potassium chloride, sodium sulfate, sodium sulfite, sodium citrate, dibasic sodium citrate, monosodium glutamate, disodium succinate, glycine, alanine, sorbitol, xylitol, inositol, sucrose, glucose, and fructose;
      ii) an insolubilizing substance, which is a salting out-type insolubilizing substance that is one or more selected from the group consisting of hydroxypropylmethylcellulose, hydroxypropylcellulose, methylcellulose, polyvinyl alcohol-polyethylene glycol graft copolymer, carboxyvinyl polymer, polyvinyl alcohol, polyethylene oxide, povidone, copolyvidone, polyoxyethylene hydrogenated castor oil, polymers containing N-isopropylacrylamide and derivatives where hydrophobic groups have been introduced to the N position of acrylamide, and polyoxyethylene polyoxypropylene glycol the range of insolubilizer in terms of the weight of the middle layer is 20 wt % or greater but less than 95 wt %; wherein the drug core is directly coated with the middle layer, wherein the middle layer is optionally precoated with one or more coating layers; and
   c) an outer layer for controlling water penetration speed that contains a water-insoluble substance, wherein said composition has a lag time within a length of 2 to 20 minutes and then the drug is quickly released, wherein the composition is in a form of a fast-disintegrating tablet.

16. The pharmaceutical composition in particle form according to claim 14 or 15, where the salting out-type insolubilizer is one or more selected from the group of substances consisting of sodium carbonate, monobasic sodium phosphate, dibasic sodium phosphate, sodium citrate, and dibasic sodium citrate.

17. The pharmaceutical composition in particle form according to claim 14 or 15, where the salting out-type insolubilizing substance is one or more selected from the group of substances consisting of hydroxypropylmethylcellulose, hydroxypropylcellulose, methylcellulose, polyvinyl alcohol-polyethylene glycol graft copolymer, polymers containing N-isopropylacrylamide and derivatives where hydrophobic groups have been introduced to the N position of acrylamide, and polyoxyethylene polyoxypropylene glycol.

18. The pharmaceutical composition according to claim 14 or 15, where the amount of coating of the middle layer is 1 to 500 wt % in terms of the weight per core containing drug.

19. The pharmaceutical composition according to claim 14 or 15, where the layer for controlling water penetration contains one or more water-insoluble substance and further, can contain one or more water-soluble substance.

20. The pharmaceutical composition according to claim 19, where the water-insoluble substance is one or more selected from the group consisting of ethylcellulose, celluloseacetate, polyvinyl acetate, celluloseacetate phthalate, carboxymethylethylcellulose, hydroxypropylmethylcellulose acetate succinate, hydroxypropylmethylcellulose phthalate, dimethylpolysiloxane, polydimethylsiloxane-silicon dioxide mixture, dimethylaminoethylmethacrylate-methylmethacrylate copolymer, methylacrylate-methacrylic acid copolymer, ethyl acrylate-methyl methacrylate copolymer emulsion, aminoalkyl methacrylate copolymer RS, dried methacrylic acid copolymer LD, aminoalkyl methacrylate copolymer E, methacrylic acid copolymer L, methacrylic acid copolymer LD, methacrylic acid copolymer S, polyvinylacetal diethylaminoacetate, casein, shellac, and zein.

21. The pharmaceutical composition in particle form according to claim 19, where the water-soluble substance is one or more selected from the group consisting of powdered acacia, sodium alginate, pregelatinized starch, sodium caseinate, carrageenan, carboxyvinyl polymer, sodium carboxymethyl starch, carmellose sodium, xanthan gum, sucrose esters of fatty acids, dextran, dextrin, lactose, hydroxypropylcellulose, hydroxypropylmethylcellulose, methylcellulose, hydroxyethylcellulose, pullulan, povidone, copolyvidone, polyoxyethylene hydrogenated castor oil, polyoxyethylene polyoxypropylene glycol, aminoalkyl methacrylate copolymer E, polyvinylacetal diethylaminoacetate, polyvinyl alcohol-polyethylene glycol graft copolymer, polyvinyl alcohol, macrogol, polyethylene oxide, glycine, alanine, aspartame, glycyrrhizinic acid, sucrose, fructose, maltose, glucose, cyclodextrin, mannitol, xylitol, maltitol, and sorbitol.

22. The pharmaceutical composition according to claim 14 or 15, where the drug contained in the particles is a drug that has an unpleasant taste.

23. The pharmaceutical composition according to claim 22, where the drug contained in the particles is solifenacin or a salt thereof, or diphenhydramine or a salt thereof.

24. The pharmaceutical composition according to claim 14 or 15, wherein said composition has a drug dissolution rate one hour after starting the dissolution test of 90 to 100% in tests using test fluid that simulates gastrointestinal fluid.

25. The pharmaceutical composition according to claim 14 or 15 wherein said composition further comprises a member selected from the group consisting of a binder, a disintegrating agent, a lubricant, a flavoring agent, a sweetener, a refrigerant, a fragrance, a coloring agent, a foaming agent, a stabilizer, an antioxidant, a preservative, and a filler.

* * * * *